United States Patent
Rosen et al.

(10) Patent No.: US 11,337,993 B2
(45) Date of Patent: May 24, 2022

(54) COMPOSITIONS AND METHODS FOR STIMULATING HAIR GROWTH

(71) Applicant: AMPLIFICA, INC., San Diego, CA (US)

(72) Inventors: David K. Rosen, San Diego, CA (US); William Rassman, San Diego, CA (US)

(73) Assignee: Amplifica, Inc., San Diego, CA (US)

( * ) Notice: Subject to any disclaimer, the term of this patent is extended or adjusted under 35 U.S.C. 154(b) by 0 days.

(21) Appl. No.: 17/410,602

(22) Filed: Aug. 24, 2021

(65) Prior Publication Data

US 2021/0386775 A1 Dec. 16, 2021

Related U.S. Application Data

(63) Continuation of application No. PCT/US2021/019522, filed on Feb. 25, 2021.

(60) Provisional application No. 62/981,480, filed on Feb. 25, 2020.

(51) Int. Cl.
| | |
|---|---|
| *A61K 31/728* | (2006.01) |
| *A61K 9/00* | (2006.01) |
| *A61K 38/19* | (2006.01) |
| *A61P 17/14* | (2006.01) |

(52) U.S. Cl.
CPC .......... *A61K 31/728* (2013.01); *A61K 9/0021* (2013.01); *A61K 38/19* (2013.01); *A61P 17/14* (2018.01)

(58) Field of Classification Search
CPC .... A61K 31/728; A61K 9/0021; A61K 38/17; A61K 38/19; A61K 2035/122; A61P 17/14
USPC .......................................................... 514/54
See application file for complete search history.

(56) References Cited

U.S. PATENT DOCUMENTS

| | | | |
|---|---|---|---|
| 5,756,094 | A | 5/1998 | Lavker et al. |
| 5,955,083 | A | 9/1999 | Bonte et al. |
| 6,103,689 | A | 8/2000 | Gilchrest |
| 2012/0034183 | A1 | 2/2012 | Cohen |
| 2015/0079137 | A1* | 3/2015 | Delgado-Gonzalez ............. A61P 43/00 424/401 |
| 2016/0317620 | A1* | 11/2016 | Alenfall ............ A61L 27/60 |
| 2017/0143605 | A1 | 5/2017 | Alenfall et al. |
| 2017/0182191 | A1* | 6/2017 | Towne ............ A61N 5/0601 |
| 2019/0000740 | A1* | 1/2019 | Wiebensjo ............ A61K 31/245 |

FOREIGN PATENT DOCUMENTS

| | | |
|---|---|---|
| WO | 2016147005 A1 | 9/2016 |
| WO | 2017032614 A1 | 3/2017 |
| WO | 2018175630 A1 | 9/2018 |

OTHER PUBLICATIONS

International Search Report for International Application No. PCT/US2021/019522 dated Jul. 15, 2021.
Written Opinion for International Application No. PCT/US2021/019522 dated Jul. 15, 2021.
Laberge et al., MTOR regulates the protumorigenic senescence-associated secretory phenotype by promoting ILIA translation. Nature cell biology, vol. 17, pp. 1049-1061, 2015.
Lay et al., FOXCI maintains the hair follicle stem cell niche and governs stern cell quiescence to preserve long-term tissue-regenerating potential. Proceedings of the National Academy of Sciences of the United States of America, vol. 113, pp. E1506-E1515, 2016.
Lee et al., Stimulation of hair follicle stem cell proliferation through an IL-1 dependent activation of gammadeltaT-cells, Elifo, vol. 6, 2017.
Li et al., RSEM: accurate transcript quantification from RNA-Seq data with or without a reference genome, BMC bioinformatics, vol. 12, 323, 2011.
Liaw et al., Altered wound healing in mice lacking a functional osteopontin gene (sppl), The Journal of clinical investigation, vol. 101, pp. 1468-1478, 1998.
Lien et al., In vivo transcriptional governance of hair follicle stern cells by canonical Wnt regulators, Nature Cell Biology, vol. 16, pp. 179-190, 2014.
Lim et al., Axin2 marks quiescent hair follicle bulge stem cells that are maintained by autocrine Wnt/beta-catenin signaling, Proceedings of the National Academy of Sciences of the United States of America, vol. 113, pp. E1498-E1505, 2016.
Liu et al., Transcriptional regulation of human osteopontin promoter by C/EBPalpha and AML-1 in metastatic cancer cells, Oncogene, vol. 23, pp. 278-288, 2004.
Lowry et al., Defining the impact of beta-catenin/Tcf transactivation on epithelial stem cells, Genes & Development, vol. 19, pp. 1596-1611, 2005.
Matsumura et al., Hair follicle aging is driven by transepidermal elimination of stem cells via COLI 7 AI proteolysis, Science, vol. 351, pp. aad4395, 2016.
Michaloglou et al., BRAFE600-associated senescence-like cell cycle arrest of human naevi, Nature, vol. 436, pp. 720-724, 2005.
Morgan, B.A. The dermal papilla: an instructive niche for epithelial stem and progenitor cells m development and regeneration of the hair follicle, Cold Spring Harbor Perspectives in Medicine, vol. 4, pp. a015180, 2014.
Morri et al., Molecular Mechanisms Linking Wound Inflammation And Fibrosis: Knockdown Of Osteopontin Leads To Rapid Repair And Reduced Scarring, The Journal Of Experimental Medicine, vol. 205, pp. 43-51, 2008.

(Continued)

*Primary Examiner* — Ganapathy Krishnan
(74) *Attorney, Agent, or Firm* — DLA Piper LLP (US)

(57) ABSTRACT

Methods and compositions for stimulating hair growth are disclosed. Compositions for stimulating hair growth include two or more of hyaluronic acid, osteopontin, and another CD44 binding ligand. Methods for stimulating hair growth include administering such composition into the skin of a patient.

29 Claims, 8 Drawing Sheets

Specification includes a Sequence Listing.

(56) References Cited

OTHER PUBLICATIONS

Mosteiro et al., Tissue Damage And Senescence Provide Critical Signals For Cellular Reprogramming In Vivo, Science, vol. 354, 2016.
Muller-Rover et al., A Comprehensive Guide For The Accurate Classification Of Murine Hair Follicles In Distinct Hair Cycle Stages, The Journal Of Investigative Dermatology, vol. 117, Mar. 15, 2001.
O'Regan et al., Osteopontin: A Key Cytokine In Cell-Mediated And Granulomatous Inflammation, International Journal Of Experimental Pathology, vol. 81, pp. 373-390, 2000.
Osaka et al., ASK.I—Dependent Recruitment And Activation Of Macrophages Induce Hair Growth In Skin Wounds, Journal of Cell Biology, vol. 176, pp. 903-909, 2007.
Pawlikowski et al., Wnt Signaling Potentiates Nevogenesis. Proceedings Of The National Academy Of Sciences Of The United States Of America, vol. 110, pp. 16009-16014, 2013.
Plikus et al. Self-Organizing And Stochastic Behaviors During The Regeneration Of Hair Stem Cells, Science. vol. 332, pp. 586-589, 2011.
Plikus et al., Macroenvironmental Regulation Of Hair Cycling And Collective Regenerative Behavior, Cold Spring Harbor Perspectives in Medicine, vol. 4, pp. a015198, 2014.
Plikus et al., Cyclic Dermal BMP Signaling Regulates Stem Cell Activation During Hair Regeneration. Nature, vol. 151, pp. 340-344, 2008.
Ponta et al., CD44: From Adhesion Molecules To Signalling Regulators. Nature Reviews Molecular Cell Biology, vol. 4, pp. 33-45, 2003.
Protin et al., CD44-Deficient Mice Develop Normally With Changes In Subpopulations And Recirculation of Lymphocyte Subsets, Journal Immunology, vol. 163, pp. 4917-4923, 1999.
Qi et al., Osteopontin Is Expressed In The Mouse Uterus During Early Pregnancy And Promotes Mouse Blastocyst Attachment And Invasion In Vitro, PloS one, vol. 9, pp. e104955, 2014.
Rendl et al., Bw1 P Signaling In Dermal Papilla Cells Is Required For Their Hair Follicle-Inductive Properties. Genes & Development, vol. 22, pp. 543-557, 2008.
Ritschka et al., The Senescence-Associated Secretory Phenotype Induces Cellular Plasticity And Tissue Regeneration, Genes & Development, vol. 31, pp. 172-183, 2017.
Robinson et al., Edger: A Bioconductor Package For Differential Expression Analysis Of Digital Gene Expression Data, Bioinformatics, vol. 26, pp. 139-140, 2010.
Roh et al., Genetics Of Melanocytic Nevi, Pigment Cell & Melanoma Research, vol. 28, pp. 661-672, 2015.
Ruhland et al., Stromal Senescence Establishes An Immunosuppressive Microenvironment That Drives Tumorigenesis, Nature Communications, vol. 7, pp. 11762, 2016.
Scadden, D.T. Nice Neighborhood: Emerging Concepts Of The Stem Cell Niche, Cell, vol. 157, pp. 41-50, 2014.
Sennett et al., Mesenchymal-Epithelial Interactions During Hair Follicle Morphogenesis And Cycling, Seminars in Cell and Developmental Biology, vol. 23, pp. 917-927, 2012.
Storer et al., Senescence Is A Developmental Mechanism That Contributes To Embryonic Growth And Patterning, Cell, vol. 155, pp. 1119-1130, 2013.
Takeda et al., Hopx Expression Defines A Subset Of Multipotent Hair Follicle Stem Cells And A Progenitor Population Primed To Give Rise To K6+ Niche Cells, Development, vol. 140, pp. 1655-1664, 2013.
Townsend et al., Tyrosinase Subcellular Distribution And Kinetic Parameters In Wild Type And C-Locus Mutant C57BL/6J Mice, The Journal Of Experimental Zoology, vol. 216, pp. 113-119, 1981.
Vidal et al., Sox9 Is Essential For Outer Root Sheath Differentiation And The Formation Of The Hair Stem Cell Compartment, Current Biology, vol. 15, pp. 1340-1351, 2005.
Wang et al., Foxcl Reinforces Quiescence In Self-Renewing Hair Follicle Stem Cells, Science, vol. 351, pp. 613-617, 2016.

Wang et al., A Multi-Scale Model For Hair Follicles Reveals Heterogeneous Domains Driving Rapid Spatiotemporal Hair Growth Patterning, Elife vol. 6, 2017.
Wang et al., Macrophages Induce AKT/Beta-Catenin-Dependent Lgr5(+) Stem Cell Activation And Hair Follicle Regeneration Through TNF, Nature Communications, vol. 8, pp. 14091, 2017.
Weber et al., Receptor-Ligand Interaction Between CD44 And Osteopontin (Eta-1), Science, vol. 271, pp. 509-512, 1996.
Xin et al., Hardwiring Stem Cell Communication Through Tissue Structure, Cell, vol. 164, pp. 1212-1225, 2016.
Xue et al., Senescence And Tumour Clearance Is Triggered By P53 Restoration In Murine Liver Carcinomas, Nature, vol. 445, pp. 656-660, 2007.
Yi et al., Mechanisms Of Quiescent Hair Follicle Stem Cell Regulation, Stem Cells, 2017.
Yoshimoto et al., Obesity-Induced Gut Microbial Metabolite Promotes Liver Cancer Through Senescence Secretome, Nature, vol. 499, pp. 97-101, 2013.
Zhang et al., Hair Follicles' Transit-Amplifying Cells Govern Concurrent Dermal Adipocyte Production Through Sonic Hedgehog, Genes & Development, vol. 30, pp. 2325-2338, 2016.
Zhou et al., Osteopontin Expression Correlates With Melanoma Invasion, Journal Of Investigative Dermatology, vol. 124, pp. 1044-1052, 2005.
Biran, A. et al., Senescent cells communicate via intercellular protein transfer, Genes & Development, vol. 29, No. 8, 2015.
Haferkamp, S. et al., Oncogene-Induced Senescence Does Not Require the pI 6INK4a or pI4ARF Melanoma Tumor Suppressors, Journal of Investigative Dermatology, vol. 129, No. 8, 2009.
Petti, C. et al., Coexpression of NRAS Q61 R and BRAF V600E in Human Melanoma Cells Activates Senescence and Increases Susceptibility to Cell-Mediated Cytotoxity, Cancer Research, vol. 66, No. 13, 2006.
Ritschka, B. et al., The senescence-associated secretory phenotype induces cellular plasticity and tissue regeneration, Genes & Development, vol. 31, No. 2, 2017.
Kunisada et al., Transgene expression of steel factor in the basal layer of epidermis promotes survival, proliferation, differentiation and migration of melanocyte precursors, Development, vol. 125, pp. 2915-2923, 1998.
Ackermann et al., Metastasizing Melanoma Formation Caused By Expression Of Activated N-Raso6lk On An INK4a-Deficient Background, Cancer Research, vol. 65, pp. 4005-4011, 2005.
Ali et al., Regulatory T Cells in Skin Facilitate Epithelial Stem Cell Differentiation, Cell, vol. 169, pp. 1119-1129 ell, 2017.
Amberg et al., Effects Of Imiquimod On Hair Follicle Stem Cells And Hair Cycle Progression, The Journal Of Investigate Dermatology, vol. 136, pp. 2140-2149, 2016.
Andriani et al., Whole Chromosome Instability Induces Senescene And Promotes SASP, Science Reports, vol. 6, pp. 35218, 2016.
Aoki et al., Conditional Deletion Of Kit In Melanocytes: White Spotting Phenotype Is Cell Autonomous, The Journal Of Investigative Dermatology, vol. 135, pp. 1829-1838, 2015.
Argyris, The Effect Of Wounds On Adjacent Growing Or Resting Hair Follicles In Mice, The Archives of Pathology & Laboratory Medicine, vol. 61, pp. 31-36, 1956.
Arnold et al., Sox2(+) Adult Stem And Progenitor Cells Are Important For Tissue Regeneration And Survival Of Mice, Cell Stem Cell, vol. 9, pp. 317-329, 2011.
Barbosa-Souza et al., Osteopontin, A Chemotactic Protein With Cytokine-Like Properties, Is Up-Regulated In Muscle Injury Caused By Bothrops Lanceolatus (Fer-De-Lance) Snake Venom, Toxicon: official journal of the International Society on Toxinology, vol. 58. pp. 398-409, 2011.
Bavik et al., The Gene Expression Program Of Prostate Fibroblast Senescence Modulates Neoplastic Epithelial Cell Proliferation Through Paracrine Mechanisms, Cancer research 66. pp. 794-802, 2006.
Blanpain et al., Plasticity of epithelial stem cells in tissue regeneration, Science, vol. 344, pp. 1242281, 2014.
Blunt et al., Defective DNA-Dependent Protein Kinase Activity Is Linked To V(D)J Recombination And DNA Repair Defects Associated With The Murine Scid Mutation, Cell, vol. 80, pp. 813-823, 1995.

(56) References Cited

OTHER PUBLICATIONS

Buback et al., Osteopontin And The Skin: Multiple Emerging Roles In Cutaneous Biology And Pathology, Experimental Dermatology, vol. 18, pp. 750-759, 2009.
Capell et al., MLL1 is Essential For The Senescene-Associated Secretory Phenotype, Genes & Development, vol. 30, pp. 321-336, 2016.
Chen et al., Organ-Level Quorum Sensing Directs Regeneration In Hair Stem Cell Populations, Cell vol. 161, pp. 277-290, 2015.
Chen et al., An RNA Interference Screen Uncovers A New Molecule In Stem Cell Self-Renewal And Long-Term Regeneration, Nature, vol. 485, pp. 104-108, 2012.
Chiche et al., Injury-Induced Senescene Enables In Vivo Reprogramming in Skeletal Muscle, Cell Stem Cell, vol. 20, pp. 407-414, pp. e404, 2017.
Choi et al., Distinct functions for Wnt/beta-catenin in hair follicle stem cell proliferation and survival and interfollicular epidermal homeostasis Cell Stem Cell, vol. 13. pp. 720-733, 2013.
Cooper et al., Wound Healing And Inflammation Genes Revealed By Array Analysis Of 'Macrophageless' PU.1 Null Mice, Genome Biology, vol. 6, 2005.
Coppe et al., The Senescence-Associated Secretory Phenotype: The Dark Side Of Tumor Suppression, Annual Review Of Pathology: Mechanisms Of Disease, vol. 5, pp. 99-118, 2010.
Coppe et al., Senescence-Associated Secretory Phenotypes Reveal Cell-Nonautonomous Functions Of Oncogenic RAS And The P53 Tumor Suppressor, PLoS Biology, vol. 6, pp. 2853-2868, 2008.
Cotsarelis et al., Label-Retaining Cells Reside In The Bulge Area Of Pilosebaceous Unit: Implications For Follicular Stem Cells, Hair Cycle, And Skin Carcinogensis, Cell, vol. 61, pp. 1329-1337, 1990.
Dankort et al., Braf(V600E) cooperates with Pten loss to induce metastatic melanoma Nature Genetics, vol. 41, pp. 544-552, 2009.
Demaria et al., An essential role for senescent cells in optimal wound healing through secretion of PDGF-AA, Dev Cell, vol. 31, pp. 722-733, 2014.
Dhomen et al., Oncogenic Braf induces melanocyte senescence and melanoma in mice. Cancer Cell, vol. 15, pp. 294-303, 2009.
Dikovskaya et al., Mitotic Stress Is an Integral Part of the Oncogene-Induced Senescence Program that Promotes Multinucleation and Cell Cycle Arrest, Cell Reports, vol. 12, pp. 1483-1496, 2015.
Dobin et al., STAR: ultrafast universal RNA-seq aligner, Bioinformatics, vol. 29, pp. 15-21, 2013.
Donati et al., Epidermal Wnt/beta-catenin signaling regulates adipocyte differentiation via secretion of adipogenic factors. Proceedings of the National Academy of Sciences of the United States of America, vol. 111, pp. E1501-E1509, 2014.
Driskell et al., Sox2-Positive Dermal Papilla Cells Specify Hair Follicle Type In Mammalian Epidermis, Development, vol. 136, pp. 2815-2823, 2009.
Eichberger et al., Foxe I, A New Transcriptional Target Of GU2 Is Expressed In Human Epidermis And Basal Cell Carcinoma. The Journal Of Investigative Dermatology, vol. 122, pp. 1180-1187, 2004.
Festa et al., Adipocyte Lineage Cells Contribute To The Skin Stem Cell Niche To Drive Hair Cycling, Cell, vol. 146, pp. 761-771, 2011.
Folgueras et al., Architectural Niche Organization By LHX2 Is Linked To Hair Follicle Stem Cell Function, Cell Stern Cell, vol. 13, pp. 314-327, 2013.
Freund et al., Inflammatory Networks During Cellular Senescence: Causes And Consequences, Trends In Molecular Medicine, vol. 16, pp. 238-246, 2010.
Gay et al. Fgf9 From Dermal Gammadelta T Cells Induces Hair Follicle Neogenesis After Wounding, Nature Medicine, vol. 19, pp. 916-923, 2013.
Giachelli et al., Evidence For A Role Of Osteopontin In Macrophage Infiltration In Response To Pathological Stimuli In Vivo, The American Journal of Pathology, vol. 152, pp. 353-358, 1998.
Greco et al., A Two-Step Mechanism For Stem Cell Activation During Hair Regeneration, Cell Stem Cell, vol. 4, pp. 155-169, 2009.
Herranz et al. MTOR Regulates MAPKAPK2 Translation To Control The Senescence-Associated Secretory Phenotype, Nature Cell Biology, vol. 17, pp. 1205-1217, 2015.
Horsley et al., NFATc1 balances quiescence and proliferation of skin stem cells, Cell, vol. 132, pp. 299-310, 2008.
Hsu et al., A family business: stem cell progeny join the niche to regulate homeostasis. Nat Rev Mol Cell Biol 13, 103-114, 2012.
Hsu et al., Emerging interactions between skin stem cells and their niches. Nat Med 20, 847-856, 2014.
Hsu et al., Dynamics between stem cells, niche, and progeny in the hair follicle. Cell 144, 92-105, 2011.
Jaks et al., Lgr5 marks cycling, yet long-lived, hair follicle stem cells. Nat Genet 40, pp. 1291-1299, 2008.
Kandyba et al., Competitive balance of intrabulge BMP/Wnt signaling reveals a robust gene network ruling stem cell homeostasis and cyclic activation. Proceedings of the National Academy of Sciences of the United States of America, vol. 110, pp. 1351-1356, 2013.
Kimura-Ueki et al., Hair cycle resting phase is regulated by cyclic epithelial FGF18 signaling, The Journal of investigative dermatology, vol. 132, pp. 1338-1345, 2012.
Kretzschmar et al., Markers of epidermal stem cell subpopulations in adult mammalian skin, Cold Cold Spring Harbor Perspectives in Medicine, vol. 4, 2014.

\* cited by examiner

```
                  10         20         30         40         50
          MRIAVICFCL LGITCAIPVK QADSGSSEEK QLYNKYPDAV ATWLNPDPSQ
              60         70         80         90        100
          KQNLLAPQNA VSSEETNDFK QETLPSKSNE SHDHMDDMDD EDDDHVDSQ
             110        120        130        140        150
          DSIDSNDSDD VDDTDDSHQS DESHHSDESD ELVTDFPTDL PATEVFTPVV
             160        170        180        190        200
          PTVDTYDGRG DSVVYGLRSK SKKFRRPDIQ YPDATDEDIT SHMESEELNG
             210        220        230        240        250
          AYKAIPVAQD LNAPSDWDSR GKDSYETSQL DDQSAETHSH KQSRLYKRRA
             260        270        280        290        300
          NDESNEHSDV IDSQELSKVS REFHSHEFHS HEDMLVVDFK SKEIDNHILKE
             310
          NISHELDSAS SEVN---C-terminal
```

Key domains are marked:

1) RGD Integrin binding domain #1 (R159-D161) - DGR
2) Integrin binding domain #2 (S162-R168) - SVVYGLR
3) Calcium binding domain (D216-S228) - DWDSRGKDSYETS
4) Thrombin cleavage site (R168-S169) - RS
5) Heparin/CD44 binding (290-305)?
5) Phosphorylation sites - S

FIG. 4

SEQUENCE LISTING

<160> NUMBER OF SEQ ID NOS: 8

<210> SEQ ID NO 1
<211> LENGTH: 27
<212> TYPE: PRT
<213> ORGANISM: homo sapiens

<400> SEQUENCE: 1

Leu Tyr Asn Lys Tyr Pro Asp Ala Val Ala Thr Trp Leu Asn Pro Asp
1               5                   10                  15

Pro Ser Gln Lys Gln Asn Leu Leu Ala Pro Gln
            20                  25

<210> SEQ ID NO 2
<211> LENGTH: 14
<212> TYPE: PRT
<213> ORGANISM: homo sapiens

<400> SEQUENCE: 2

Asn Ala Val Ser Ser Glu Glu Thr Asn Asp Phe Lys Gln Glu
1               5                   10

<210> SEQ ID NO 3
<211> LENGTH: 7
<212> TYPE: PRT
<213> ORGANISM: homo sapiens

<400> SEQUENCE: 3

Ser Val Val Tyr Gly Leu Arg
1               5

<210> SEQ ID NO 4
<211> LENGTH: 7
<212> TYPE: PRT
<213> ORGANISM: homo sapiens

<400> SEQUENCE: 4

Glu Leu Val Thr Asp Phe Pro
1               5

<210> SEQ ID NO 5
<211> LENGTH: 7
<212> TYPE: PRT
<213> ORGANISM: homo sapiens

<400> SEQUENCE: 5

Ser Leu Ala Tyr Gly Leu Arg
1               5

<210> SEQ ID NO 6
<211> LENGTH: 298
<212> TYPE: PRT
<213> ORGANISM: homo sapiens

<400> SEQUENCE: 6

Ile Pro Val Lys Gln Ala Asp Ser Gly Ser Glu Glu Lys Gln Leu
1               5                   10                  15

Tyr Asn Lys Tyr Pro Asp Ala Val Ala Thr Trp Leu Asn Pro Asp Pro
                20                  25                  30

Ser Gln Lys Gln Asn Leu Leu Ala Pro Gln Asn Ala Val Ser Ser Glu
            35                  40                  45

Glu Thr Asn Asp Phe Lys Gln Glu Thr Leu Pro Ser Lys Ser Asn Glu
50                  55                  60

Ser His Asp His Met Asp Asp Met Asp Glu Asp Asp Asp His
65                  70                  75                  80

Val Asp Ser Gln Asp Ser Ile Asp Ser Asn Asp Ser Asp Val Asp
                85                  90                  95

Asp Thr Asp Asp Ser His Gln Ser Asp Glu Ser His His Ser Asp Glu
                100                 105                 110

Ser Asp Glu Leu Val Thr Asp Phe Pro Thr Asp Leu Pro Ala Thr Glu
            115                 120                 125

Val Phe Thr Pro Val Val Pro Thr Val Asp Thr Tyr Asp Gly Arg Gly
        130                 135                 140

Asp Ser Val Val Tyr Gly Leu Arg Ser Lys Ser Lys Lys Phe Arg Arg
145                 150                 155                 160

Pro Asp Ile Gln Tyr Pro Asp Ala Thr Asp Glu Asp Ile Thr Ser His
                165                 170                 175

Met Glu Ser Glu Glu Leu Asn Gly Ala Tyr Lys Ala Ile Pro Val Ala
            180                 185                 190

Gln Asp Leu Asn Ala Pro Ser Asp Trp Asp Ser Arg Gly Lys Asp Ser
        195                 200                 205

Tyr Glu Thr Ser Gln Leu Asp Asp Gln Ser Ala Glu Thr His Ser His
    210                 215                 220

Lys Gln Ser Arg Leu Tyr Lys Arg Lys Ala Asn Asp Glu Ser Asn Glu
225                 230                 235                 240

His Ser Asp Val Ile Asp Ser Gln Glu Leu Ser Lys Val Ser Arg Glu
                245                 250                 255

Phe His Ser His Glu Phe His Ser His Glu Asp Met Leu Val Val Asp
            260                 265                 270

Pro Lys Ser Lys Glu Glu Asp Lys His Leu Lys Phe Arg Ile Ser His
        275                 280                 285

Glu Leu Asp Ser Ala Ser Ser Glu Val Asn
    290                 295

<210> SEQ ID NO 7

```
<211> LENGTH: 314
<212> TYPE: PRT
<213> ORGANISM: homo sapiens

<400> SEQUENCE: 7

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Asn Ala Val Ser Ser Glu
        50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
                85                  90                  95

Val Asp Ser Gln Asp Ser Ile Asp Ser Asn Asp Ser Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
        130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 8
<211> LENGTH: 13
<212> TYPE: PRT
<213> ORGANISM: homo sapiens

<400> SEQUENCE: 8

Asp Trp Asp Ser Arg Gly Lys Asp Ser Tyr Glu Thr Ser
1               5                   10
```

COMPOSITIONS AND METHODS FOR STIMULATING HAIR GROWTH

CROSS-REFERENCE TO RELATED APPLICATION

This application is a continuation of International Patent Application No. PCT/US2021/019522 filed on Feb. 25, 2021, which claims priority to U.S. Provisional Patent Application No. 62/981,480 filed on Feb. 25, 2020, each of which are hereby incorporated by reference in its entirety.

BACKGROUND OF THE INVENTION

The present invention generally relates to compositions and methods for stimulating hair growth.

Hair loss often has a negative social and psychological impact on the individual suffering therefrom. Many factors are believed to contribute to hair loss, including genetics, hormones, environmental exposure, medications, psychological stress, and nutrition. One known treatment is hair transplantation, which requires anesthesia, is costly, time-consuming, and sometimes painful. Other approaches include massage and acupuncture, but these have not been shown to be effective. Hormones and other drugs have been used to treat hair loss, however these treatments frequently cause undesirable side effects, such as hair growth in unwanted areas. Accordingly, there is a need for an effective therapy for stimulating hair growth.

BRIEF SUMMARY OF THE INVENTION

In one embodiment a composition for stimulating hair growth includes osteopontin and hyaluronic acid. The hyaluronic acid may have an average molecular weight in a range of about 20 KDa to 1350 KDa. The hyaluronic acid may be cross linked, and in some embodiments may have a cross-link density of about 20% or greater. In some embodiments the hyaluronic acid is present in a concentration of 25 mcg/mL or greater, or between about 25 mcg/mL and about 100 mcg/mL. In some embodiments the composition may also include one or more of serglycin, chondroitin sulfate, fibrin, IGFBP4, and GFP10, and in particular may include one or more of serglycin, chondroitin sulfate, and fibrin. In some embodiments the composition may include a hyaluronidase inhibitor, for example, selected from high molecular mass poly(styrene-4-sulfonate) (PSS), gossypol, sodium aurothiomalate, fenoprofen, glycerrhizic acid, fatty acids, plant-derived compounds, heparin, and 0-sulfated HA (sHA) or combinations thereof.

In another embodiment, a composition for stimulating hair growth includes hyaluronic acid and one or more of serglycin, chondroitin sulfate, fibrin, IGFBP4, and GFP10. In particular, the composition may include one or more of serglycin, chondroitin sulfate, and fibrin. The hyaluronic acid may have an average molecular weight in a range of about 20 KDa to 1350 KDa. The hyaluronic acid may be cross linked, and in some embodiments may have a cross-link density of about 20% or greater. In some embodiments the hyaluronic acid is present in a concentration of 25 mcg/mL or greater, or between about 25 mcg/mL and about 100 mcg/mL. In some embodiments the composition may also include osteopontin. In some embodiments the composition may also include a hyaluronidase inhibitor, for example, selected from high molecular mass poly(styrene-4-sulfonate) (PSS), gossypol, sodium aurothiomalate, fenoprofen, glycerrhizic acid, fatty acids, plant-derived compounds, heparin, and O-sulfated HA (sHA) or combinations thereof.

In an embodiment, a method of stimulating hair growth in a skin of a patient in need thereof, includes administering a composition comprising hyaluronic acid and a CD44-binding ligand to the skin of the patient. In some embodiments administering includes applying the composition to a surface of the skin, while in other embodiments administering includes injecting the composition into a dermal layer of the skin. The composition may be injected about 400 microns to about 2 mm deep into the skin. In some embodiments the composition is administered in a plurality of injections in an amount of about 400 injections/cm$^2$ skin to about 650 injections/cm$^2$ skin. In some embodiments the needle is a microneedle. In some embodiments the composition may be encased in a liposome, for example a liposome comprising hydrogenated phospholipids.

In some embodiments a method of stimulating hair growth further includes applying iontophoresis to the skin.

In some embodiments a method of stimulating hair growth further includes applying electroporation to the skin.

In some embodiments a method of stimulating hair growth further includes applying laser ablation to the skin.

In some embodiments a method of stimulating hair growth further includes applying radiofrequency thermal ablation to the skin.

In some embodiments a method of stimulating hair growth further includes applying a microneedle device to the skin.

In an embodiment, a method of administering a composition for hair growth to a patient in need of treatment for hair loss includes injecting the composition into a skin of the patient, wherein the composition comprises hyaluronic acid and a CD44-binding ligand. The composition may be injected via a needle, for example, where the needle is inserted 400 microns to about 2 mm into the skin before injection. In some embodiments the needle is a microneedle. In some embodiments the composition may be encased in a liposome, for example a liposome comprising hydrogenated phospholipids.

In an embodiment, a composition for stimulating hair growth includes two or more of osteopontin, hyaluronic acid, serglycin, chondroitin sulfate, fibrin, IGFBP4, and GFP10.

In some embodiments, a composition for stimulating hair growth comprising hyaluronic acid in a concentration of about 1 mcg/mL to about 250 mcg/mL. The hyaluronic acid may have an average molecular weight, for example, in a range of about 4,000 Da to 10,000 Da, in a range of about 10,000 Da to about 100,000 Da, in a range of about 15 kDa to about 50 kDa, in a range of about 75 kDa to about 350 kDa, or in a range of about 20 kDa to 1350 kDa. In some embodiments, hyaluronic acid has an average molecular weight greater than about 950 kDa.

In some embodiments of the composition, the hyaluronic acid is cross-linked. For example, the hyaluronic acid may have a cross-link density of about 20% or greater.

In some embodiments of the composition, the hyaluronic acid is present in a concentration of about 25 mcg/mL to about 250 mcg/mL, about 25 mcg/mL to about 100 mcg/mL, about 100 mcg/mL to about 250 mcg/mL, or about 100 ug/mL or less.

In some embodiments, a composition for stimulating hair growth comprising hyaluronic acid in a concentration of about 250 mcg/mL or less further comprises one or more of osteopontin, hyaluronic acid, serglycin, chondroitin sulfate, fibrin, IGFBP4, and GFP10.

In some embodiments of the invention, a method of stimulating hair growth in a skin of a patient in need thereof includes administering a composition comprising hyaluronic acid in a concentration of about 1 mcg/mL to about 250 mcg/mL to the skin of the patient. In such methods, administering may include injecting the composition into a dermal layer of the skin, for example about 400 microns to about 2 mm deep into the skin. In other such methods, administering may include injecting a plurality of injections in an amount of about 400 injections/cm$^2$ skin to about 650 injections/cm$^2$ skin. In some embodiments a method further includes a further step, such as applying iontophoresis to the skin, applying electroporation to the skin, applying laser ablation to the skin, applying radiofrequency thermal ablation to the skin, and/or applying a microneedle device to the skin. In some embodiments the composition further includes a CD44-binding ligand, for example osteopontin.

In some embodiments of the invention a method of administering a composition for hair growth to a patient in need of treatment for hair loss includes injecting the composition into a skin of the patient, wherein the composition comprises hyaluronic acid in a concentration of about 1 mcg/mL to about 250 mcg/mL. In some embodiments the composition is injected via a needle, for example wherein the needle is inserted 400 microns to about 2 mm into the skin before injection. In some embodiments the needle is a microneedle. In some embodiments the composition further comprises a CD44-binding ligand, for example osteopontin.

BRIEF DESCRIPTION OF THE SEVERAL VIEWS OF THE DRAWINGS

The following detailed description of embodiments of the compositions and methods for stimulating hair growth will be better understood when read in conjunction with the appended drawings. It should be understood, however, that the invention is not limited to the precise arrangements shown.

In the drawings:

FIG. 4 illustrates osteopontin sequence and domains. SEQ ID NO: 3 represents integrin binding domain #2 (amino acid residues 162-168) of osteopontin; SEQ ID NO: 7 represents the calcium binding domain (amino acid residues 216-228) of osteopontin; SEQ ID NO: 8 represents the sequence of osteopontin including the signal peptide (amino acid residues 1-16).

DETAILED DESCRIPTION OF THE INVENTION

Figure 1:
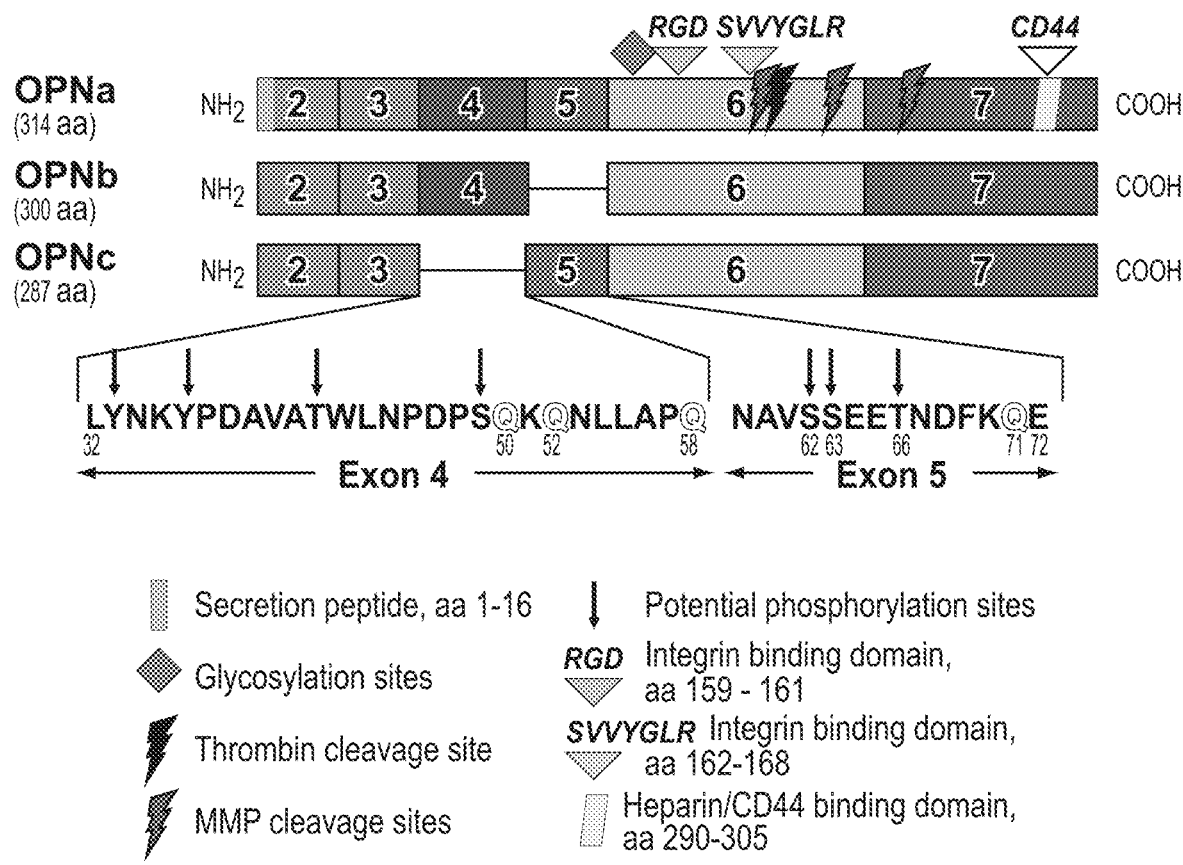
FIG. 1 illustrates osteopontin sequence and domains. SEQ ID NO: 1 represents amino acids of Exon 4 of osteopontin; SEQ ID NO: 2 represents amino acid residues of Exon 5 of osteopontin; SEQ ID NO: 3 represents integrin binding domain #2 (amino acid residues 162-168) of osteopontin.
Figure 2:
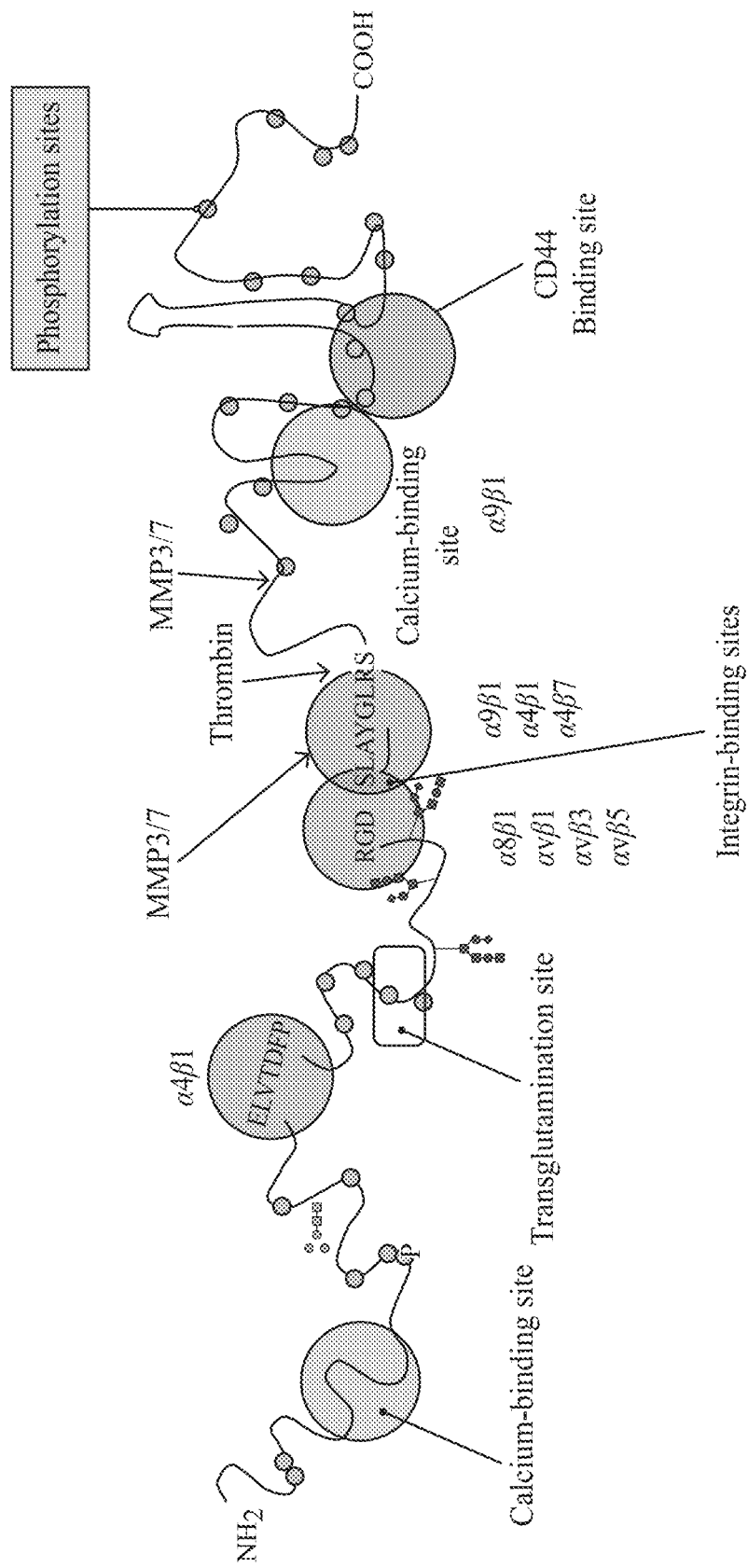
FIG. 2 illustrates osteopontin domains and structure; SEQ ID NO: 4 represents an integrin binding site of osteopontin; SEQ ID NO: 5 represents an integrin binding site of osteopontin.
Figure 3:
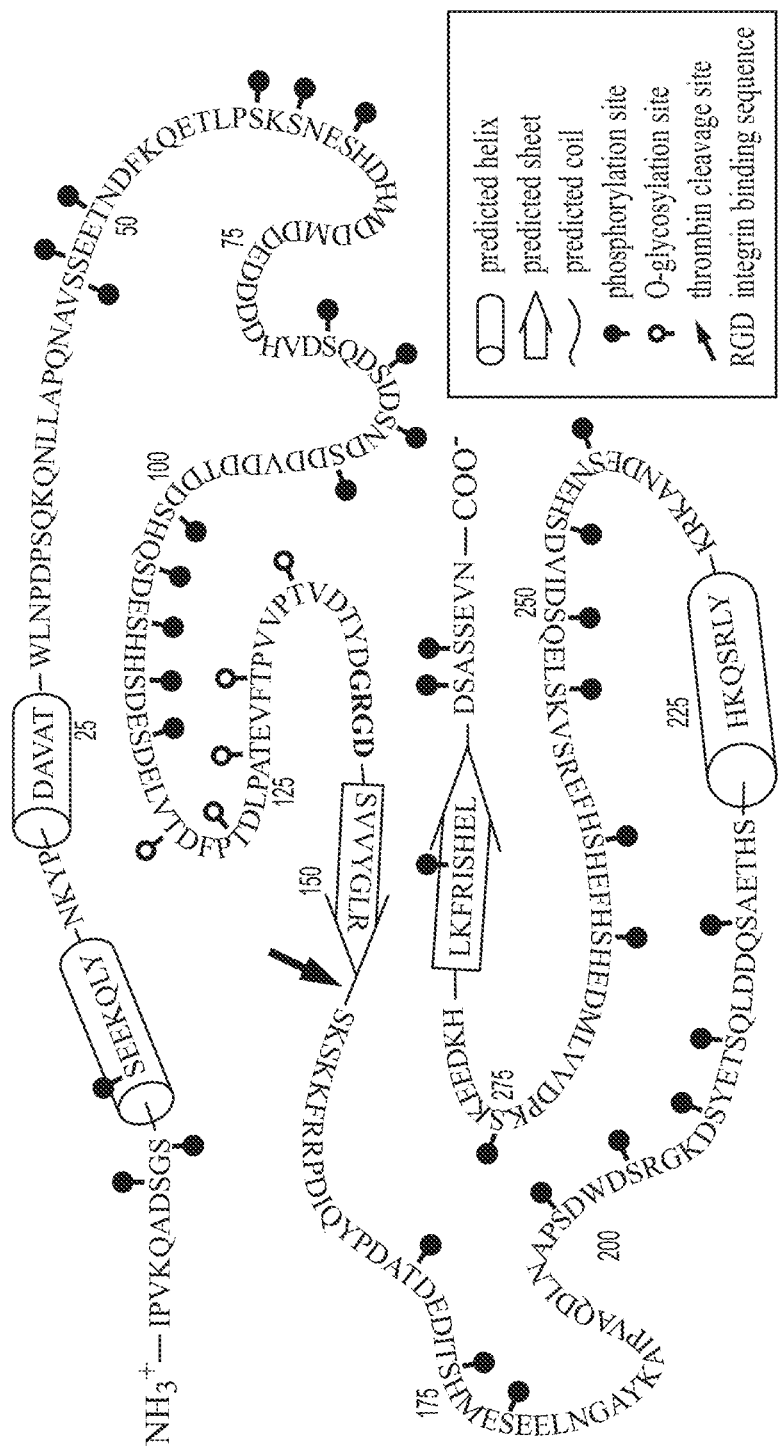
FIG. 3 illustrates osteopontin domains and structure. SEQ ID NO: 6 represents amino acids residues 17-314 of osteopontin.

The present invention provides methods and compositions useful for stimulating hair growth.

I. Compositions

In some embodiments a hair growth stimulating composition includes a naturally occurring ligand for CD44, or a fragment or derivative thereof.

In some embodiments, the naturally occurring ligand for CD44 is one or more of osteopontin (OPN, SPP1), serglycin (SRGN), chondroitin sulfate, collagen, fibronectin, fibrin, or a CD44-binding fragment, isoform, or derivative thereof.

CD44-binding fragments, isoforms, or derivatives of a naturally occurring ligand for CD44 include synthetic peptides that bind CD44 and are generated on the basis of CD44-binding domains of osteopontin, serglycin, chondroitin sulfate, collagen, fibronectin, and/or fibrin.

In some embodiments a hair growth stimulating composition includes hyaluronic acid.

In some embodiments a hair growth stimulating composition includes one or more naturally occurring ligands for CD44, or a fragment or derivative thereof, and hyaluronic acid.

In some embodiments, a hair growth stimulating composition includes a combination of two or more of hyaluronic acid, osteopontin, serglycin, chondroitin sulfate, collagen, fibronectin, fibrin, and proteolytically- or synthetically-produced CD44-binding fragments, isoforms, or derivatives thereof. In some embodiments, a hair growth composition includes three or more of hyaluronic acid, osteopontin, serglycin, chondroitin sulfate, collagen, fibronectin, fibrin, and CD44-binding proteolytically- or synthetically-produced fragments, isoforms, or derivatives thereof. Any of the above may also include hyaluronidase inhibitor and/or one or more other constituents.

Various nonlimiting embodiments include the compositions described in the following table, wherein an "X" indicates the component is included in the embodiment of the invention:

| Composition number | Osteopontin | Serglycin | Chondroitin Sulfate | Fibrin | Hyaluronic acid | Hyaluronidase inhibitor |
|---|---|---|---|---|---|---|
| 1 | X | | | | | |
| 2 | X | X | | | | |
| 3 | X | | X | | | |
| 4 | X | | | X | | |
| 5 | X | | | | X | |
| 6 | X | | | | | X |

-continued

| Composition number | Osteopontin | Serglycin | Chondroitin Sulfate | Fibrin | Hyaluronic acid | Hyaluronidase inhibitor |
|---|---|---|---|---|---|---|
| 7 | | X | | | | |
| 8 | | X | X | | | |
| 9 | | X | | X | | |
| 10 | | X | | | X | |
| 11 | | X | | | | X |
| 12 | | | X | | | |
| 13 | | | X | X | | |
| 14 | | | X | | X | |
| 15 | | | X | | | X |
| 16 | | | | X | | |
| 17 | | | | X | X | |
| 18 | | | | X | | X |
| 19 | | | | | X | |
| 20 | | | | | X | X |
| 21 | | | | | | X |
| 22 | X | X | X | | | |
| 23 | X | X | | X | | |
| 24 | X | X | | | X | |
| 25 | X | X | | | | X |
| 26 | X | | X | X | | |
| 27 | X | | X | | X | |
| 28 | X | | X | | | X |
| 29 | X | | | X | X | |
| 30 | X | | | X | | X |
| 31 | X | | | | X | X |
| 32 | X | | | | | |
| 33 | | X | X | X | | |
| 34 | | X | X | | X | |
| 35 | | X | X | | | X |
| 36 | | X | | X | X | |
| 37 | | X | | X | | X |
| 38 | | X | | | X | X |
| 39 | | | X | X | X | |
| 40 | | | X | | X | X |
| 41 | | | | X | X | X |
| 42. | X | X | X | X | | |
| 43. | X | X | X | | X | |
| 44. | X | X | X | | | X |
| 45. | X | X | | X | X | |
| 46. | X | X | | X | | X |
| 47. | X | X | | | X | X |
| 48. | X | | X | X | X | |
| 49. | X | | X | X | | X |
| 50. | X | | X | | X | X |
| 51. | X | | | X | X | X |
| 52. | | X | X | X | X | |
| 53. | | X | X | X | | X |
| 54. | | X | X | | X | X |
| 55. | X | X | | X | X | X |
| 56. | X | X | X | X | | X |
| 57. | X | X | X | | X | X |
| 58. | X | X | | X | X | X |
| 59. | X | | X | X | X | X |
| 60. | | X | X | X | X | X |
| 61. | X | X | X | X | X | X |

In some embodiments a composition for stimulating hair growth may include one or more ligands of CD44. Such ligands may include osteopontin. Other ligands included in the scope of the invention include serglycin, chondroitin sulfate (e.g., chondroitin 4-sulfate), collagen, fibronectin, fibrin, an insulin growth factor binding protein (IGFBP) (e.g., IGFBP-1, IGFBP-2, IGFBP-3, IGFBP4, IGFBP-5, and IGFBP-6), a green fluorescent protein, and hyaluronic acid.

In some embodiments a composition may include a fragment, isoform, or derivative of a ligand of CD44, wherein such fragment, isoform, or derivative has at least 95% identity, at least 90% identity, at least 85% identity, at least 80% identity, at least 75% identity, at least 70% identity, at least 65% identity or at least 60% identity with the corresponding ligand of CD44.

In some embodiments a composition comprises about 0.01 wt % or greater CD44 binding ligand, about 0.025 wt % or greater CD44 binding ligand, about 0.050 wt % or greater CD44 binding ligand, about 0.075 wt % or greater CD44 binding ligand, about 0.1 wt % or greater CD44 binding ligand, about 0.25 wt % or greater CD44 binding ligand, about 0.5 wt % or greater CD44 binding ligand, about 0.75 wt % or greater CD44 binding ligand, about 1 wt % or greater CD44 binding ligand, about 2.5 wt % or greater CD44 binding ligand, about 5 wt % or greater CD44 binding ligand, about 7.5 wt % or greater CD44 binding ligand, or about 10 wt % or greater CD44 binding ligand. In some embodiments a composition comprises between about 0.01 wt % and about 0.025 wt % CD44 binding ligand, between about 0.025 wt % and about 0.05 wt % CD44 binding ligand, between about 0.025 wt % and about 0.075 wt % CD44 binding ligand, between about 0.025 wt % and about 0.1 wt % CD44 binding ligand, between about 0.01 wt % and about 0.1 wt % CD44 binding ligand, between about 0.05 wt % and about 0.075 wt % CD44 binding ligand, between about 0.05 wt % and about 0.1 wt % CD44 binding ligand, between about 0.075 wt % and about 0.1 wt % CD44 binding ligand, between about 0.1 wt % and about 0.2 wt % CD44 binding ligand, between about 0.1 wt % and about 0.5 wt % CD44 binding ligand, between about 0.2 wt % and about 0.4 wt % CD44 binding ligand, between about 0.5 wt % and about 1 wt % CD44 binding ligand, between about 0.4 wt % and about 0.6 wt % CD44 binding ligand, between about 0.6 and about 0.8 wt % CD44 binding ligand, between about 0.8 wt % and about 1 wt % CD44 binding ligand, between about 1 wt % and about 2 wt % CD44 binding ligand, between about 1 wt % and about 5 wt % CD44 binding ligand, between about 2 wt % and about 4 wt % CD44 binding ligand, between about 5 wt % and about 10 wt % CD44 binding ligand, between about 4 wt % and about 6 wt % CD44 binding ligand, between about 6 and about 8 wt % CD44 binding ligand, or between about 8 wt % and about 10 wt % CD44 binding ligand.

1. Osteopontin

Osteopontin is an extracellular signaling protein that is a natural ligand for CD44. FIGS. 1-4 describe the sequence and domain structure of osteopontin. Without being bound by theory, it is believed that osteopontin may induce CD44 activation by proteolytically cleaving CD44 resulting in the intra-cellular release of the CD44 intracellular domain (ICD). The CD44-ICD is then free to go into the nucleus and modulate gene expression. Osteopontin is discussed in International Patent Publication No. WO 2018175630, which is hereby incorporated by reference in its entirety.

In some embodiments a composition useful for stimulating hair growth includes osteopontin, or a CD44 binding fragment, isoform, or derivative thereof. In some embodiments a CD44 binding fragment, isoform or derivative of osteopontin includes a peptide that is produced by proteolytic cleavage of a naturally occurring (e.g., full-length) osteopontin protein. In some embodiments a CD44 binding fragment, isoform, or derivative of osteopontin comprises residues 290-305 of osteopontin, 291-304 of osteopontin, comprises residues 292-303 of osteopontin, comprises residues 293-302 of osteopontin, comprises residues 294-301 of osteopontin, or comprises residues 295-300 of osteopontin. In some embodiments, a CD44 binding fragment, isoform, or derivative of osteopontin comprises SEQ ID NO. 2. In some embodiments, a CD44 binding fragment, isoform, or derivative of osteopontin comprises SEQ ID NO. 3.

In some embodiments a composition comprises about 0.01 wt % or greater osteopontin, about 0.025 wt % or greater osteopontin or CD44 binding fragment, isoform, or derivative thereof, about 0.050 wt % or greater osteopontin or CD44 binding fragment, isoform, or derivative thereof, about 0.075 wt % or greater osteopontin or CD44 binding fragment, isoform, or derivative thereof, about 0.1 wt % or greater osteopontin or CD44 binding fragment, isoform, or derivative thereof, about 0.25 wt % or greater osteopontin or CD44 binding fragment, isoform, or derivative thereof, about 0.5 wt % or greater osteopontin or CD44 binding fragment, isoform, or derivative thereof, about 0.75 wt % or greater osteopontin or CD44 binding fragment, isoform, or derivative thereof, about 1 wt % or greater osteopontin or CD44 binding fragment, isoform, or derivative thereof, about 2.5 wt % or greater osteopontin or CD44 binding fragment, isoform, or derivative thereof, about 5 wt % or greater osteopontin or CD44 binding fragment, isoform, or derivative thereof, about 7.5 wt % or greater osteopontin or CD44 binding fragment, isoform, or derivative thereof, or about 10 wt % or greater osteopontin or CD44 binding fragment, isoform, or derivative thereof. In some embodiments a composition comprises between about 0.01 wt % and about 0.025 wt % osteopontin or CD44 binding fragment, isoform, or derivative thereof, between about 0.025 wt % and about 0.05 wt % osteopontin or CD44 binding fragment, isoform, or derivative thereof, between about 0.025 wt % and about 0.075 wt % osteopontin or CD44 binding fragment, isoform, or derivative thereof, between about 0.025 wt % and about 0.1 wt % osteopontin or CD44 binding fragment, isoform, or derivative thereof, between about 0.01 wt % and about 0.1 wt % osteopontin or CD44 binding fragment, isoform, or derivative thereof, between about 0.05 wt % and about 0.075 wt % osteopontin or CD44 binding fragment, isoform, or derivative thereof, between about 0.05 wt % and about 0.1 wt % osteopontin or CD44 binding fragment, isoform, or derivative thereof, between about 0.075 wt % and about 0.1 wt % osteopontin or CD44 binding fragment, isoform, or derivative thereof, between about 0.1 wt % and about 0.2 wt % osteopontin or CD44 binding fragment, isoform, or derivative thereof, between about 0.1 wt % and about 0.5 wt % osteopontin or CD44 binding fragment, isoform, or derivative thereof, between about 0.2 wt % and about 0.4 wt % osteopontin or CD44 binding fragment, isoform, or derivative thereof, between about 0.5 wt % and about 1 wt % osteopontin or CD44 binding fragment, isoform, or derivative thereof, between about 0.4 wt % and about 0.6 wt % osteopontin or CD44 binding fragment, isoform, or derivative thereof, between about 0.6 and about 0.8 wt % osteopontin or CD44 binding fragment, isoform, or derivative thereof, between about 0.8 wt % and about 1 wt % osteopontin or CD44 binding fragment, isoform, or derivative thereof, between about 1 wt % and about 2 wt % osteopontin or CD44 binding fragment, isoform, or derivative thereof, between about 1 wt % and about 5 wt % osteopontin or CD44 binding fragment, isoform, or derivative thereof, between about 2 wt % and about 4 wt % osteopontin or CD44 binding fragment, isoform, or derivative thereof, between about 5 wt % and about 10 wt % osteopontin or CD44 binding fragment, isoform, or derivative thereof, between about 4 wt % and about 6 wt % osteopontin or CD44 binding fragment, isoform, or derivative thereof, between about 6 and about 8 wt % osteopontin or CD44 binding fragment, isoform, or derivative thereof, or between about 8 wt % and about 10 wt % osteopontin or CD44 binding fragment, isoform, or derivative thereof.

2. Other Ligands for CD44

In some embodiments a composition useful for stimulating hair growth includes one or more ligands for CD44 other than or in addition to osteopontin. Such ligands include serglycin, chondroitin sulfate (e.g., chondroitin 4-sulfate), collagen, fibronectin, fibrin, an insulin growth factor binding protein (IGFBP) (e.g., IGFBP-1, IGFBP-2, IGFBP-3, IGFBP4, IGFBP-5, and IGFBP-6), and a green fluorescent protein (e.g., GFP10). Another ligand for CD44 is hyaluronic acid, discussed further below. In some embodiments, the composition comprises IGFBP4 and GFP10).

Without being bound by theory, it is believed that each of these components may serve as a ligand that binds to CD44. In some embodiments, a composition useful for stimulating hair growth includes a ligand that binds to CD44. In some embodiments a composition useful for stimulating hair growth includes a combination of two or more (e.g., three or four) ligands that bind to CD44.

a. Serglycin

In some embodiments a composition comprises about 0.01 wt % or greater serglycin, about 0.025 wt % or greater serglycin, about 0.050 wt % or greater serglycin, about 0.075 wt % or greater serglycin, about 0.1 wt % or greater serglycin, about 0.25 wt % or greater serglycin, about 0.5 wt % or greater serglycin, about 0.75 wt % or greater serglycin, about 1 wt % or greater serglycin, about 2.5 wt % or greater serglycin, about 5 wt % or greater serglycin, about 7.5 wt % or greater serglycin, or about 10 wt % or greater serglycin. In some embodiments a composition comprises between about 0.01 wt % and about 0.025 wt % serglycin, between about 0.025 wt % and about 0.05 wt % serglycin, between about 0.025 wt % and about 0.075 wt % serglycin, between about 0.025 wt % and about 0.1 wt % serglycin, between about 0.01 wt % and about 0.1 wt % serglycin, between about 0.05 wt % and about 0.075 wt % serglycin, between about 0.05 wt % and about 0.1 wt % serglycin, between about 0.075 wt % and about 0.1 wt % serglycin, between about 0.1 wt % and about 0.2 wt % serglycin, between about 0.1 wt % and about 0.5 wt % serglycin, between about 0.2 wt % and about 0.4 wt % serglycin, between about 0.5 wt % and about 1 wt % serglycin, between about 0.4 wt % and about 0.6 wt % serglycin, between about 0.6 and about 0.8 wt % serglycin, between about 0.8 wt % and about 1 wt % serglycin, between about 1 wt % and about 2 wt % serglycin, between about 1 wt % and about 5 wt % serglycin, between about 2 wt % and about 4 wt % serglycin, between about 5 wt % and about 10 wt % serglycin, between about 4 wt % and about 6 wt % serglycin, between about 6 and about 8 wt % serglycin, or between about 8 wt % and about 10 wt % serglycin.

b. Chondroitin

In some embodiments a composition comprises chondroitin or a salt thereof, e.g., chondroitin sulfate. In some embodiments a composition comprises about 0.01 wt % or greater chondroitin or a salt thereof, about 0.025 wt % or greater chondroitin or a salt thereof, about 0.050 wt % or greater chondroitin or a salt thereof, about 0.075 wt % or greater chondroitin or a salt thereof, about 0.1 wt % or greater chondroitin or a salt thereof, about 0.25 wt % or greater chondroitin or a salt thereof, about 0.5 wt % or greater chondroitin or a salt thereof, about 0.75 wt % or greater chondroitin or a salt thereof, about 1 wt % or greater chondroitin or a salt thereof, about 2.5 wt % or greater chondroitin or a salt thereof, about 5 wt % or greater chondroitin or a salt thereof, about 7.5 wt % or greater chondroitin or a salt thereof, or about 10 wt % or greater chondroitin or a salt thereof. In some embodiments a composition comprises between about 0.01 wt % and about 0.025 wt % chondroitin or a salt thereof, between about 0.025 wt % and about 0.05 wt % chondroitin or a salt thereof, between about 0.025 wt % and about 0.075 wt % chondroitin or a salt thereof, between about 0.025 wt % and about 0.1 wt % chondroitin or a salt thereof, between about 0.01 wt % and about 0.1 wt % chondroitin or a salt thereof, between about 0.05 wt % and about 0.075 wt % chondroitin or a salt thereof, between about 0.05 wt % and about 0.1 wt % chondroitin or a salt thereof, between about 0.075 wt % and about 0.1 wt % chondroitin or a salt thereof, between about 0.1 wt % and about 0.2 wt % chondroitin or a salt thereof, between about 0.1 wt % and about 0.5 wt % chondroitin or a salt thereof, between about 0.2 wt % and about 0.4 wt % chondroitin or a salt thereof, between about 0.5 wt % and about 1 wt % chondroitin or a salt thereof, between about 0.4 wt % and about 0.6 wt % chondroitin or a salt thereof, between about 0.6 and about 0.8 wt % chondroitin or a salt thereof, between about 0.8 wt % and about 1 wt % chondroitin or a salt thereof, between about 1 wt % and about 2 wt % chondroitin or a salt thereof, between about 1 wt % and about 5 wt % chondroitin or a salt thereof, between about 2 wt % and about 4 wt % chondroitin or a salt thereof, between about 5 wt % and about 10 wt % chondroitin or a salt thereof, between about 4 wt % and about 6 wt % chondroitin or a salt thereof, between about 6 and about 8 wt % chondroitin or a salt thereof, or between about 8 wt % and about 10 wt % chondroitin or a salt thereof.

c. Fibrin

In some embodiments a composition comprises about 0.01 wt % or greater fibrin, about 0.025 wt % or greater fibrin, about 0.050 wt % or greater fibrin, about 0.075 wt % or greater fibrin, about 0.1 wt % or greater fibrin, about 0.25 wt % or greater fibrin, about 0.5 wt % or greater fibrin, about 0.75 wt % or greater fibrin, about 1 wt % or greater fibrin, about 2.5 wt % or greater fibrin, about 5 wt % or greater fibrin, about 7.5 wt % or greater fibrin, or about 10 wt % or greater fibrin. In some embodiments a composition comprises between about 0.01 wt % and about 0.025 wt % fibrin, between about 0.025 wt % and about 0.05 wt % fibrin, between about 0.025 wt % and about 0.075 wt % fibrin, between about 0.025 wt % and about 0.1 wt % fibrin, between about 0.01 wt % and about 0.1 wt % fibrin, between about 0.05 wt % and about 0.075 wt % fibrin, between about 0.05 wt % and about 0.1 wt % fibrin, between about 0.075 wt % and about 0.1 wt % fibrin, between about 0.1 wt % and about 0.2 wt % fibrin, between about 0.1 wt % and about 0.5 wt % fibrin, between about 0.2 wt % and about 0.4 wt % fibrin, between about 0.5 wt % and about 1 wt % fibrin, between about 0.4 wt % and about 0.6 wt % fibrin, between about 0.6 and about 0.8 wt % fibrin, between about 0.8 wt % and about 1 wt % fibrin, between about 1 wt % and about 2 wt % fibrin, between about 1 wt % and about 5 wt % fibrin, between about 2 wt % and about 4 wt % fibrin, between about 5 wt % and about 10 wt % fibrin, between about 4 wt % and about 6 wt % fibrin, between about 6 and about 8 wt % fibrin, or between about 8 wt % and about 10 wt % fibrin.

d. Collagen

In some embodiments a composition comprises about 0.01 wt % or greater collagen, about 0.025 wt % or greater collagen, about 0.050 wt % or greater collagen, about 0.075 wt % or greater collagen, about 0.1 wt % or greater collagen, about 0.25 wt % or greater collagen, about 0.5 wt % or greater collagen, about 0.75 wt % or greater collagen, about 1 wt % or greater collagen, about 2.5 wt % or greater collagen, about 5 wt % or greater collagen, about 7.5 wt % or greater collagen, or about 10 wt % or greater collagen. In some embodiments a composition comprises between about 0.01 wt % and about 0.025 wt % collagen, between about 0.025 wt % and about 0.05 wt % collagen, between about 0.025 wt % and about 0.075 wt % collagen, between about 0.025 wt % and about 0.1 wt % collagen, between about 0.01 wt % and about 0.1 wt % collagen, between about 0.05 wt % and about 0.075 wt % collagen, between about 0.05 wt % and about 0.1 wt % collagen, between about 0.075 wt % and about 0.1 wt % collagen, between about 0.1 wt % and about 0.2 wt % collagen, between about 0.1 wt % and about 0.5 wt % collagen, between about 0.2 wt % and about 0.4 wt % collagen, between about 0.5 wt % and about 1 wt % collagen, between about 0.4 wt % and about 0.6 wt % collagen, between about 0.6 and about 0.8 wt % collagen, between about 0.8 wt % and about 1 wt % collagen, between about 1 wt % and about 2 wt % collagen, between about 1 wt % and about 5 wt % collagen, between about 2 wt % and about 4 wt % collagen, between about 5 wt % and about 10 wt % collagen, between about 4 wt % and about 6 wt % collagen, between about 6 and about 8 wt % collagen, or between about 8 wt % and about 10 wt % collagen.

e. Fibronectin

In some embodiments a composition comprises about 0.01 wt % or greater fibronectin, about 0.025 wt % or greater fibronectin, about 0.050 wt % or greater fibronectin, about 0.075 wt % or greater fibronectin, about 0.1 wt % or greater fibronectin, about 0.25 wt % or greater fibronectin, about 0.5 wt % or greater fibronectin, about 0.75 wt % or greater fibronectin, about 1 wt % or greater fibronectin, about 2.5 wt % or greater fibronectin, about 5 wt % or greater fibronectin, about 7.5 wt % or greater fibronectin, or about 10 wt % or greater fibronectin. In some embodiments a composition comprises between about 0.01 wt % and about 0.025 wt % fibronectin, between about 0.025 wt % and about 0.05 wt % fibronectin, between about 0.025 wt % and about 0.075 wt % fibronectin, between about 0.025 wt % and about 0.1 wt % fibronectin, between about 0.01 wt % and about 0.1 wt % fibronectin, between about 0.05 wt % and about 0.075 wt % fibronectin, between about 0.05 wt % and about 0.1 wt % fibronectin, between about 0.075 wt % and about 0.1 wt % fibronectin, between about 0.1 wt % and about 0.2 wt % fibronectin, between about 0.1 wt % and about 0.5 wt % fibronectin, between about 0.2 wt % and about 0.4 wt % fibronectin, between about 0.5 wt % and about 1 wt % fibronectin, between about 0.4 wt % and about 0.6 wt % fibronectin, between about 0.6 and about 0.8 wt % fibronectin, between about 0.8 wt % and about 1 wt % fibronectin, between about 1 wt % and about 2 wt % fibronectin, between about 1 wt % and about 5 wt % fibronectin, between about 2 wt % and about 4 wt % fibronectin, between about 5 wt % and about 10 wt % fibronectin, between about 4 wt % and about 6 wt % fibronectin, between about 6 and about 8 wt % fibronectin, or between about 8 wt % and about 10 wt % fibronectin.

f. Insulin-like growth factor-binding protein

In some embodiments a composition comprises about 0.01 wt % or greater insulin-like growth factor-binding protein, about 0.025 wt % or greater insulin-like growth factor-binding protein, about 0.050 wt % or greater insulin-like growth factor-binding protein, about 0.075 wt % or greater insulin-like growth factor-binding protein, about 0.1 wt % or greater insulin-like growth factor-binding protein, about 0.25 wt % or greater insulin-like growth factor-binding protein, about 0.5 wt % or greater insulin-like growth factor-binding protein, about 0.75 wt % or greater insulin-like growth factor-binding protein, about 1 wt % or greater insulin-like growth factor-binding protein, about 2.5 wt % or greater insulin-like growth factor-binding protein, about 5 wt % or greater insulin-like growth factor-binding protein, about 7.5 wt % or greater insulin-like growth factor-binding protein, or about 10 wt % or greater insulin-like growth factor-binding protein. In some embodiments a composition comprises between about 0.01 wt % and about 0.025 wt % insulin-like growth factor-binding protein, between about 0.025 wt % and about 0.05 wt % insulin-like growth factor-binding protein, between about 0.025 wt % and about 0.075 wt % insulin-like growth factor-binding protein, between about 0.025 wt % and about 0.1 wt % insulin-like growth factor-binding protein, between about 0.01 wt % and about 0.1 wt % insulin-like growth factor-binding protein, between about 0.05 wt % and about 0.075 wt % insulin-like growth factor-binding protein, between about 0.05 wt % and about 0.1 wt % insulin-like growth factor-binding protein, between about 0.075 wt % and about 0.1 wt % insulin-like growth factor-binding protein, between about 0.1 wt % and about 0.2 wt % insulin-like growth factor-binding protein, between about 0.1 wt % and about 0.5 wt % insulin-like growth factor-binding protein, between about 0.2 wt % and about 0.4 wt % insulin-like growth factor-binding protein, between about 0.5 wt % and about 1 wt % insulin-like growth factor-binding protein, between about 0.4 wt % and about 0.6 wt % insulin-like growth factor-binding protein, between about 0.6 and about 0.8 wt % insulin-like growth factor-binding protein, between about 0.8 wt % and about 1 wt % insulin-like growth factor-binding protein, between about 1 wt % and about 2 wt % insulin-like growth factor-binding protein, between about 1 wt % and about 5 wt % insulin-like growth factor-binding protein, between about 2 wt % and about 4 wt % insulin-like growth factor-binding protein, between about 5 wt % and about 10 wt % insulin-like growth factor-binding protein, between about 4 wt % and about 6 wt % insulin-like growth factor-binding protein, between about 6 and about 8 wt % insulin-like growth factor-binding protein, or between about 8 wt % and about 10 wt % insulin-like growth factor-binding protein.

g. Green Fluorescent Protein

In some embodiments a composition comprises about 0.01 wt % or greater green fluorescent protein, about 0.025 wt % or greater green fluorescent protein, about 0.050 wt % or greater green fluorescent protein, about 0.075 wt % or greater green fluorescent protein, about 0.1 wt % or greater green fluorescent protein, about 0.25 wt % or greater green fluorescent protein, about 0.5 wt % or greater green fluorescent protein, about 0.75 wt % or greater green fluorescent protein, about 1 wt % or greater green fluorescent protein, about 2.5 wt % or greater green fluorescent protein, about 5 wt % or greater green fluorescent protein, about 7.5 wt % or greater green fluorescent protein, or about 10 wt % or greater green fluorescent protein. In some embodiments a composition comprises between about 0.01 wt % and about 0.025 wt % green fluorescent protein, between about 0.025 wt % and about 0.05 wt % green fluorescent protein, between about 0.025 wt % and about 0.075 wt % green fluorescent protein, between about 0.025 wt % and about 0.1 wt % green fluorescent protein, between about 0.01 wt % and about 0.1 wt % green fluorescent protein, between about 0.05 wt % and about 0.075 wt % green fluorescent protein, between about 0.05 wt % and about 0.1 wt % green fluorescent protein, between about 0.075 wt % and about 0.1 wt % green fluorescent protein, between about 0.1 wt % and about 0.2 wt % green fluorescent protein, between about 0.1 wt % and about 0.5 wt % green fluorescent protein, between about 0.2 wt % and about 0.4 wt % green fluorescent protein, between about 0.5 wt % and about 1 wt % green fluorescent protein, between about 0.4 wt % and about 0.6 wt % green fluorescent protein, between about 0.6 and about 0.8 wt % green fluorescent protein, between about 0.8 wt % and about 1 wt % green fluorescent protein, between about 1 wt % and about 2 wt % green fluorescent protein, between about 1 wt % and about 5 wt % green fluorescent protein, between about 2 wt % and about 4 wt % green fluorescent protein, between about 5 wt % and about 10 wt % green fluorescent protein, between about 4 wt % and about 6 wt % green fluorescent protein, between about 6 and about 8 wt % green fluorescent protein, or between about 8 wt % and about 10 wt % green fluorescent protein.

3. Hyaluronic Acid

In some embodiments a composition useful for stimulating hair growth includes hyaluronic acid. Hyaluronic acid is a natural ligand for CD44 and it has now been found to be pro-inflammatory and stimulate hair growth. Hyaluronic acid is a natural linear polymer containing repeated units of a disaccharide of β-1,4-D-glucuronic acid and β-1,3-N-acetyl-D-glucosamine, as shown in formula I:

Formula I

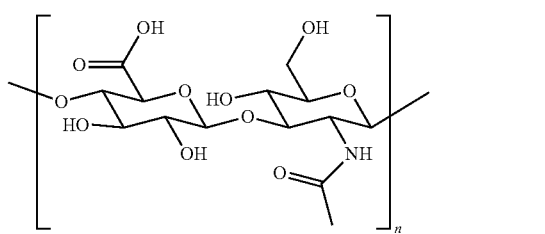

In some embodiments the hyaluronic acid has a low average molecular weight, which as used herein refers to ranges from about 15,000 Da to about 40,000 Da. In some embodiments the hyaluronic acid has an intermediate average molecular weight, which as used herein refers to ranges from about 75,000 Da to about 350,000 Da. In some embodiments the hyaluronic acid has a high average molecular weight, which as used herein refers to about 950,000 Da and greater.

In some embodiments the hyaluronic acid has an average molecular weight ranging from about 4,000 Da or less to about 10,000 Da. In some embodiments the hyaluronic acid has an average molecular weight ranging from about 10,000 Da to about 100,000 Da. In some embodiments the hyaluronic acid has an average molecular weight ranging from about 100,000 Da to about 1,500,000 Da or greater.

In some embodiments hyaluronic acid has an average molecular weight between about 1 kDA and about 10 kDA, between about 10 kDa and about 50 kDA, between about 50 kDa and about 100 kDA, between about 100 kDa and about 150 kDA, between about 200 kDa and about 250 kDA, between about 300 kDa and about 350 kDA, between about 400 kDa and about 450 kDA, between about 500 kDa and about 550 kDA, between about 600 kDa and about 650 kDA, between about 700 kDa and about 750 kDA, between about 800 kDa and about 850 kDA, between about 900 kDa and about 1000 kDA, between about 1000 kDa and about 1100 kDA, between about 1100 kDa and about 1200 kDA, between about 1200 kDa and about 1300 kDA, between about 1300 kDa and about 1400 kDA, between about 1400 kDa and about 1500 kDA, between about 1 kDa and about 100 kDA, between about 100 kDa and about 250 kDA, between about 250 kDa and about 500 kDA, between about 500 kDa and about 750 kDA, between about 750 kDa and about 1000 kDA, between about 1000 kDa and about 1250 kDA, between about 1250 kDa and about 1500 kDA, between about 1 kDa and about 250 kDA, between about 1 kDa and about 500 kDA, between about 100 kDa and about 500 kDA, between about 250 kDa and about 750 kDA, between about 500 kDa and about 1000 kDA, between about 750 kDa and about 1250 kDA, or between about 1000 kDa and about 1500 kDA.

In some embodiments the hyaluronic acid is cross-linked. Cross-linking may improve the lifetime of the hyaluronic acid and in some embodiments, some degree of cross-linking can be desirable. In some embodiments the hyaluronic acid has sufficient cross-linking to last for about a week. However, without being bound by a mechanism of action, it is believed that hyaluronic acid is effective in stimulating hair growth by interacting with CD44 receptors. Accordingly, it is desirable that the hyaluronic acid is not cross-linked so extensively that the cross-linking interferes with the ability of the hyaluronic acid to interact with a CD44 receptor.

The hydroxyl (—OH), carboxylic (—COOH), and/or amide (—NHCOCH$_3$) functional groups of hyaluronic acid can cross link via an ether bond (R—O—R), ester linkage (R—COO—R), or carbodiimide, respectively. In some embodiments hyaluronic acid is cross-linked with 1-ethyl-3-(3-dimethylaminopropyl) carbodiimide (EDC), glutaraldehyde (GTA), poly (ethylene glycol) diglycidil ether (PEGDE), ethylene glycol diglycidil ether (EGDE), divinyl sulfonate (DVS), or pentaerythritol tetra-acrulate (PT).

The hyaluronic acid may have a cross-link density of about $1\times10^{-7}$ mol/cm$^3$ or greater, about $2\times10^{-7}$ mol/cm$^3$ or greater, about $3\times10^{-7}$ mol/cm$^3$ or greater, about $4\times10^{-7}$ mol/cm$^3$ or greater, about $5\times10^{-7}$ mol/cm$^3$ or greater, about $6\times10^{-7}$ mol/cm$^3$ or greater, about $7\times10^{-7}$ mol/cm$^3$ or greater, about $8\times10^{-7}$ mol/cm$^3$ or greater, about $9\times10^{-7}$ mol/cm$^3$ or greater, about $1\times10^{-6}$ mol/cm$^3$ or greater, about $2\times10^{-6}$ mol/cm$^3$ or greater, about $3\times10^{-6}$ mol/cm$^3$ or greater, about $4\times10^{-6}$ mol/cm$^3$ or greater, about $5\times10^{-6}$ mol/cm$^3$ or greater, about $6\times10^{-6}$ mol/cm$^3$ or greater, about $7\times10^{-6}$ mol/cm$^3$ or greater, about $8\times10^{-6}$ mol/cm$^3$ or greater, about $9\times10^{-6}$ mol/cm$^3$ or greater, or about $1\times10^{-5}$ mol/cm$^3$ or greater. In some embodiments the hyaluronic acid may have a cross-link density between about $1\times10^{-7}$ mol/cm$^3$ and about $1\times10^{-5}$ mol/cm$^3$, between about $1\times10^{-7}$ mol/cm$^3$ and about $1\times10^{-6}$ mol/cm$^3$, between about $1\times10^{-7}$ mol/cm$^3$ and about $5\times10^{-7}$ mol/cm$^3$, between about $5\times10^{-7}$ mol/cm$^3$ and about $1\times10^{-6}$ mol/cm$^3$, between about $1\times10^{-7}$ mol/cm$^3$ and about $2\times10^{-7}$ mol/cm$^3$, between about $2\times10^{-7}$ mol/cm$^3$ and about $4\times10^{-7}$ mol/cm$^3$, between about $4\times10^{-7}$ mol/cm$^3$ and about $6\times10^{-7}$ mol/cm$^3$, between about $6\times10^{-7}$ mol/cm$^3$ and about $8\times10^{-7}$ mol/cm$^3$, or between about $8\times10^{-7}$ mol/cm$^3$ and about $1\times10^{-6}$ mol/cm$^3$, between about $1\times10^{-6}$ mol/cm$^3$ and about $1\times10^{-5}$ mol/cm$^3$, between about $1\times10^{-6}$ mol/cm$^3$ and about $5\times10^{-6}$ mol/cm$^3$, between about $5\times10^{-6}$ mol/cm$^3$ and about $1\times10^{-5}$ mol/cm$^3$, between about $1\times10^{-6}$ mol/cm$^3$ and about $2\times10^{-6}$ mol/cm$^3$, between about $2\times10^{-7}$ mol/cm$^3$ and about $4\times10^{-7}$ mol/cm$^3$, between about $4\times10^{-7}$ mol/cm$^3$ and about $6\times10^{-7}$ mol/cm$^3$, between about $6\times10^{-7}$ mol/cm$^3$ and about $8\times10^{-7}$ mol/cm$^3$, between about $8\times10^{-7}$ mol/cm$^3$ and about $1\times10^{-5}$ mol/cm$^3$, or between about $5\times10^{-7}$ mol/cm$^3$ and about $5\times10^{-6}$ mol/cm$^3$.

Compositions of the invention may include an amount of hyaluronic acid sufficient to provide a therapeutic effect, for example stimulating hair growth in a patient in need thereof. However, higher concentrations of hyaluronic acid may result in undesirable inflammation. In some embodiments compositions of the invention include an amount of hyaluronic acid sufficient to provide a therapeutic effect, for example stimulating hair growth in a patient in need thereof, and insufficient to provide an unacceptable inflammatory response. As used throughout this description, both mcg/mL and μg/mL refer to micrograms per milliliter. In some embodiments hyaluronic acid is present in an amount of about 10 mcg/mL of composition or greater, about 15 mcg/mL of composition or greater, about 20 mcg/mL of composition or greater, about 25 mcg/mL of composition or greater, about 30 mcg/mL of composition or greater, about 35 mcg/mL of composition or greater, about 40 mcg/mL of composition or greater, about 45 mcg/mL of composition or greater, about 50 mcg/mL of composition or greater, about 55 mcg/mL of composition or greater, about 60 mcg/mL of composition or greater, about 65 mcg/mL of composition or greater, about 70 mcg/mL of composition or greater, about 75 mcg/mL of composition or greater, about 80 mcg/mL of composition or greater, about 85 mcg/mL of composition or greater, about 90 mcg/mL of composition or greater, about 95 mcg/mL of composition or greater, or about 100 mcg/mL of composition or greater.

In some embodiments hyaluronic acid is present in an amount in a range of about 1 mcg/mL of composition to about 250 mcg/mL of composition, about 10 mcg/mL of composition to about 250 mcg/mL of composition, about 10 mcg/mL of composition to about 200 mcg/mL of composition, 10 mcg/mL of composition to about 150 mcg/mL of composition, 10 mcg/mL of composition to about 100 mcg/mL of composition, about 25 mcg/mL of composition to about 250 mcg/mL of composition, about 25 mcg/mL of composition to about 200 mcg/mL of composition, about 25 mcg/mL of composition to about 150 mcg/mL of composition, about 25 mcg/mL of composition to about 100 mcg/mL of composition, about 50 mcg/mL of composition to about 250 mcg/mL of composition, about 50 mcg/mL of composition to about 200 mcg/mL of composition, about 50 mcg/mL of composition to about 150 mcg/mL of composition, about 50 mcg/mL of composition to about 100 mcg/mL of composition, about 75 mcg/mL of composition to about 250 mcg/mL of composition, about 75 mcg/mL of composition to about 200 mcg/mL of composition, about 75 mcg/mL of composition to about 150 mcg/mL of composition, about 75 mcg/mL of composition to about 100 mcg/mL of composition, about 100 mcg/mL of composition to about 250 mcg/mL of composition, about 100 mcg/mL of composition to about 200 mcg/mL of composition, about 100 mcg/mL of composition to about 150 mcg/mL of composition, about 150 mcg/mL of composition to about 250 mcg/mL of composition, about 200 mcg/mL of composition to about 250 mcg/mL of composition, about 60 mcg/mL of composition to about 80 mcg/mL of composition, about 50 mcg/mL of composition to about 75 mcg/mL of composition, about 25 mcg/mL of composition to about 75 mcg/mL of composition, about 10 mcg/mL of composition to about 50 mcg/mL of composition, or about 10 mcg/mL of composition to about 25 mcg/mL of composition.

In some embodiments a composition comprises about 0.001 wt % or greater hyaluronic acid, about 0.0025 wt % or greater hyaluronic acid, about 0.0050 wt % or greater hyaluronic acid, about 0.0075 wt % or greater hyaluronic acid, about 0.01 wt % or greater hyaluronic acid, about 0.025 wt % or greater hyaluronic acid, about 0.05 wt % or greater hyaluronic acid, about 0.075 wt % or greater hyaluronic acid, about 0.1 wt % or greater hyaluronic acid, about 0.25 wt % or greater hyaluronic acid, about 0.5 wt % or greater hyaluronic acid, about 0.75 wt % or greater hyaluronic acid, or about 1 wt % or greater hyaluronic acid. In some embodiments a composition comprises between about 0.001 wt % and about 0.0025 wt % hyaluronic acid, between about 0.0025 wt % and about 0.005 wt % hyaluronic acid, between about 0.0025 wt % and about 0.0075 wt % hyaluronic acid, between about 0.0025 wt % and about 0.01 wt % hyaluronic acid, between about 0.001 wt % and about 0.01 wt % hyaluronic acid, between about 0.005 wt % and about 0.0075 wt % hyaluronic acid, between about 0.005 wt % and about 0.01 wt % hyaluronic acid, between about 0.0075 wt % and about 0.01 wt % hyaluronic acid, between about 0.01 wt % and about 0.02 wt % hyaluronic acid, between about 0.01 wt % and about 0.05 wt % hyaluronic acid, between about 0.02 wt % and about 0.04 wt % hyaluronic acid, between about 0.05 wt % and about 0.1 wt % hyaluronic acid, between about 0.04 wt % and about 0.06 wt % hyaluronic acid, between about 0.06 and about 0.08 wt % hyaluronic acid, between about 0.08 wt % and about 0.1 wt % hyaluronic acid, between about 0.1 wt % and about 0.2 wt % hyaluronic acid, between about 0.1 wt % and about 0.5 wt % hyaluronic acid, between about 0.2 wt % and about 0.4 wt % hyaluronic acid, between about 0.5 wt % and about 1 wt % hyaluronic acid, between about 0.4 wt % and about 0.6 wt % hyaluronic acid, between about 0.6 and about 0.8 wt % hyaluronic acid, or between about 0.8 wt % and about 1 wt % hyaluronic acid.

In some embodiments, a composition according to an embodiment of the invention comprises a commercially available hyaluronic acid composition. For example, suitable commercially available hyaluronic acid compositions include, but are not limited to, hyaluronic acids sold under the trademarks JUVEDERM™, RESTYLANE-L™, CAPTIQUE™, BELOTERO BALANCE™, PREVELLE SILK™, ELEVESS™, HYLAFORM™, EUFLEXXA™, GEL-ONE™ HYALGAN™ ORTHOVISC™, MONOVISC™ SUPARTZ™, SYNVISC™ AND SYNVISC-ONE™.

C. Hyaluronidase Inhibitor

In some embodiments according to the invention, a composition includes a hyaluronidase inhibitor. Examples of hyaluronidase inhibitors include, but are not limited to, high molecular mass poly (styrene-4-sulfonate) (PSS), gossypol, sodium aurothiomalate, fenoprofen, glycerrhizic acid, heparin, and O-sulfated hyaluronic acid (sHA), and dextran sulfate, or combinations thereof.

In some embodiments a composition comprises about 0.01 wt % or greater hyaluronidase inhibitor, about 0.025 wt % or greater hyaluronidase inhibitor, about 0.050 wt % or greater hyaluronidase inhibitor, about 0.075 wt % or greater hyaluronidase inhibitor, about 0.1 wt % or greater hyaluronidase inhibitor, about 0.25 wt % or greater hyaluronidase inhibitor, about 0.5 wt % or greater hyaluronidase inhibitor, about 0.75 wt % or greater hyaluronidase inhibitor, about 1 wt % or greater hyaluronidase inhibitor, about 2.5 wt % or greater hyaluronidase inhibitor, about 5 wt % or greater hyaluronidase inhibitor, about 7.5 wt % or greater hyaluronidase inhibitor, or about 10 wt % or greater hyaluronidase inhibitor. In some embodiments a composition comprises between about 0.01 wt % and about 0.025 wt % hyaluronidase inhibitor, between about 0.025 wt % and about 0.05 wt % hyaluronidase inhibitor, between about 0.025 wt % and about 0.075 wt % hyaluronidase inhibitor, between about 0.025 wt % and about 0.1 wt % hyaluronidase inhibitor, between about 0.01 wt % and about 0.1 wt % hyaluronidase inhibitor, between about 0.05 wt % and about 0.075 wt % hyaluronidase inhibitor, between about 0.05 wt % and about 0.1 wt % hyaluronidase inhibitor, between about 0.075 wt % and about 0.1 wt % hyaluronidase inhibitor, between about 0.1 wt % and about 0.2 wt % hyaluronidase inhibitor, between about 0.1 wt % and about 0.5 wt % hyaluronidase inhibitor, between about 0.2 wt % and about 0.4 wt % hyaluronidase inhibitor, between about 0.5 wt % and about 1 wt % hyaluronidase inhibitor, between about 0.4 wt % and about 0.6 wt % hyaluronidase inhibitor, between about 0.6 and about 0.8 wt % hyaluronidase inhibitor, between about 0.8 wt % and about 1 wt % hyaluronidase inhibitor, between about 1 wt % and about 2 wt % hyaluronidase inhibitor, between about 1 wt % and about 5 wt % hyaluronidase inhibitor, between about 2 wt % and about 4 wt % hyaluronidase inhibitor, between about 5 wt % and about 10 wt % hyaluronidase inhibitor, between about 4 wt % and about 6 wt % hyaluronidase inhibitor, between about 6 and about 8 wt % hyaluronidase inhibitor, or between about 8 wt % and about 10 wt % hyaluronidase inhibitor.

D. Carrier and Other Additives

In some embodiments a composition includes a carrier medium. Such carrier medium may be a biocompatible fluid suitable for injection into a mammalian skin. In some embodiments the carrier medium comprises a saline solution. In some embodiments hyaluronic acid serves as the carrier medium as well as an active ingredient.

In some embodiments a composition includes one or more additives. Such additives may include a preservative or a biocide.

In some embodiments a composition includes a microemulsfier, a nanoemulsifier, a solid lipid nanoparticle, a nanostructured lipid carrier, a liposome or a vesicle.

In some embodiments a composition may comprise a fatty acid (e.g., oleic acid), ester of a fatty acid and alcohol (e.g., isopropyl myristate, isopropyl palmitate, ethyl oleate), medium chain triglycerides, triacetin, or a terpene (e.g., limonene, methol, cinoele). In some embodiments a composition may comprise a surfactants. For example, suitable surfactants include, but are not limited to, TWEEN™ (polysorbates), CREMOPHOR™ (mixture of macrogol glycerol hydroxystearate, PEG-40 castor oil, polyoxyl 40 hydrogenated castor oil), TRANSCUTOL™ P (diethylene glycol monoethyl ether), PLUROL OLEIQUE™ (polyglyceryl-3-oleate), PLUROL ISOSTEARIQUE™ (isostearic acid ester of poly-glycerols and higher oligomers) and LABRASOL™ (mixture of mono-, di- and tri-glycerides of C8 and C10 fatty acids, and mono- and di-esters of PEG), and lecithin. In some embodiments a composition may comprise a cosurfactant. For example, suitable cosurfactants include, but are not limited to short and medium chain alcohols and polyglyceryl derivatives, including ethanol, isopropanol, isopropyl myristate and propylene glycol.

In some embodiments a composition comprises one or more of soybean oil, jojoba oil, aloe vera oil, soybean phosphatidylcholine, water, polysorbate 80, ethanol, benzyl alcohol, isopropyl alcohol, glycerine, glyceryl monostearate, propylene glycol.

II. Methods

Methods of Production

A process for the production of a therapeutic composition according to an embodiment of the invention comprises mixing an effective amount of active agents. In some embodiments an effective amount of hyaluronic acid is mixed with an effective amount of osteopontin. In some embodiments, the hyaluronic acid has average molecular weight in a range of about 4,000 Da to 10,000 Da, in a range of about 10,000 Da to about 100,000 Da, in a range of about 15 kDa to about 50 kDa, in a range of about 75 kDa to about 350 kDa, or in a range of about 20 kDa to 1350 kDa. In some embodiments, hyaluronic acid has an average molecular weight greater than about 950 kDa. In some embodiments an effective amount of hyaluronic acid is mixed with an effective amount of CD44-binding ligand. In some embodiments an effective amount of osteopontin is mixed with an effective amount of CD44-binding ligand. In some embodiments effective amounts, respectively, of hyaluronic acid and osteopontin are mixed with an effective amount of CD44-binding ligand. In some embodiments of compositions according to the invention, an effective amounts of hyaluronidase inhibitor is mixed with one or more of hyaluronic acid, osteopontin, and CD44-binding ligand. Said processes may also include a step of preparing a physiologically acceptable carrier medium, to which the active agents are added. Preferably, the physiologically acceptable carrier medium is injectable.

In some embodiments a method of production includes a step of forming a microemulsion or a nanoemulsion. A microemulstion or nanoemulsion may comprise oil, water, surfactant and cosurfactant to form a colloidal dispersion of droplet sizes in a range of about 10 nm to about 100 nm. In some embodiments a microemulsion or nanoemulsion may comprise a fatty acid (e.g., oleic acid), ester of a fatty acid and alcohol (e.g., isopropyl myristate, isopropyl palmitate, ethyl oleate), medium chain triglycerides, triacetin, or a terpene (e.g., limonene, methol, cinoele). In some embodiments a microemulsion or nanoemulsion may comprise a surfactants. For example, suitable surfactants include, but are not limited to, TWEEN™ (polysorbates), CREMOPHOR™ (mixture of macrogol glycerol hydroxystearate, PEG-40 castor oil, polyoxyl 40 hydrogenated castor oil), TRANSCUTOL™ P (diethylene glycol monoethyl ether), PLUROL OLEIQUE™ (polyglyceryl-3-oleate), PLUROL ISOSTEARIQUE™ (isostearic acid ester of poly-glycerols and higher oligomers) and LABRASOL™ (mixture of mono-, di- and tri-glycerides of C8 and C10 fatty acids, and mono- and di-esters of PEG), and lecithin. In some embodiments a microemulsion or nanoemulsion may comprise a cosurfactant. For example, suitable cosurfactants include, but are not limited to short and medium chain alcohols and polyglyceryl derivatives, including ethanol, isopropanol, isopropyl myristate and propylene glycol. In some embodiments formation of a microemulsion or nanoemulsion includes use of a high-pressure homogenizer, microfluidizer and/or ultrasonicator.

In some embodiments a method of production includes a step of mixing a composition according to an embodiment of the invention with a solid nanoparticle. A solid nanoparticle may comprise an inorganic material such as a metal oxide (e.g., zinc oxide, titanium dioxide) or polymers that are solid at room temperature.

In some embodiments a method of production includes a step of mixing a composition according to an embodiment of the invention with a solid lipid nanoparticle. A solid lipid nanoparticle may comprise a lipid that is solid at room temperature with a surface covering of surfactant to stabilize them as droplets having a size of less than about 100 nm when dispersed in water.

In some embodiments a method of production includes a step of mixing a composition according to an embodiment of the invention with a nanostructured lipid carrier. A nanostructured lipid carrier may comprise a fluid lipid phase embedded into a solid lipid matrix or localized at the surface of solid platelets and the surfactant layer.

In some embodiments a method of production includes a step of mixing a composition according to an embodiment of the invention with a liposome. A liposome may comprise a spherical vesicles composed of amphiphilic phospholipids and cholesterol, self-associated into multilamellar, large unilamellar and small unilamellar vesicles.

In some embodiments a method of production includes a step of mixing a composition according to an embodiment of the invention with a flexible vesicle. A flexible vesicle may comprise a material that will associate into bilayer structures as well as components that confer flexibility. In some embodiments a flexible vesicle comprises an ethosome (i.e., a phospholipid with a high proportion of ethanol), a niosome (i.e., non-ionic surfactant), an invasome (i.e., phospholipids, ethanol, and a mixture of terpene penetration enhancer), an SECosomes (i.e., surfactant, ethanol, and cholesterol), or a PEV (i.e., penetration enhancer vesicle). In some embodiments a PEV may comprise oleic acid, limonene, or propylene glycol.

In some embodiments a method of production includes a step of mixing a composition according to an embodiment of the invention with a polymeric micelle or polymeric dendrimer. A polymeric micelle may be a colloidal carrier with a hydrophilic exterior shell and a hydrophobic interior core. A polymeric micelle may be nanosized. A polymeric dendrimer may comprise a branched polymer structure.

In some embodiments any of the above-described CD44-binding fragments, isoforms, or derivatives of a naturally occurring ligand for CD44 areproteolytically produced, while in other embodiments such are synthetically produced.

Methods of Administration

A method of administering a composition according to an embodiment of the invention comprises delivery of a composition according to an embodiment of the invention to a hair follicle. In some embodiments the delivery is effected by topical administration, that is, application of the composition to the surface of the skin and allowing the composition to permeate the skin. In some embodiments a method of administration includes a step to enhance permeation prior to topical administration of a composition. In some embodiments the delivery is effected by injection into the skin.

In some embodiments, topical delivery is performed following, or in conjunction with, application of iontophoresis. For example, iontophoreses may comprise application of a mild electric current (e.g., 0.1 to 1.0 mA/cm$^2$) to increase skin permeation of the composition. Without being bound by theory, it is believed iontophoresis may improve permeation of the skin by electromigration, electroosmosis, and/or enhanced passive diffusion.

In some embodiments, topical delivery is performed following, or in conjunction with, application of electroporation. For example, electroporation may comprise application of high intensity, high voltage (e.g., 50-1500 V) electric pulses of short duration (10 microseconds to 10 milliseconds) to form aqueous pores in the lipid bilayers of the stratum corneum of the skin.

In some embodiments, topical delivery is performed following, or in conjunction with, application of sonophoresis. For example, sonophoresis may comprise application of acoustic waves at high frequency (e.g. about 500 kHz to 1250 kHz) or low frequency (e.g., about 20 to about 100 kHz) or (beginning with one of high or low frequency and progressing to the other of high or low frequency).

In some embodiments, topical delivery is performed following, or in conjunction with, application of laser ablation. Laser ablation may comprise generation of a photomechanical wave by laser ablation of a target material (e.g., polymer) placed on the surface of the skin.

In some embodiments, topical delivery is performed following, or in conjunction with, magnetophoresis. Magnetophoresis may comprise application of a magnetic field, for example pulsed electromagnetic fields, to the skin.

In some embodiments, topical delivery is performed following application of radiofrequency thermal ablation. Thermal ablation may comprise application of extreme heat (e.g., about 300° C. for microseconds) at the skin surface. Without being bound by theory, it is believed that thermal ablation may vaporize portions of the stratum corneum to create micron-scale channels. Thermal ablation may be accomplished with commercially available devices including VIADOR™ (Syneron Medical Ltd, Israel) and PASSPORT' (Nitto-Denko, Japan). In some embodiments thermal ablation may be accomplished with an erbium:yttrium-gallium-garnet (Er:YAG) emitting at 2,790 nm or yttrium scandium gallium garnet (YSGG) laser emitting at 2,940 nm. In some embodiments fractional laser ablation may be applied to sub-mm regions to generate spots mimicking a microneedle array-type pattern (e.g., 40-300 μm with densities between 50-600 cm').

In some embodiments, topical delivery is performed following application of microneedle device.

A method for administering a composition according to an embodiment of the invention comprises injecting a therapeutic amount of composition in the skin of a patient in need of treatment. In some embodiments a composition according to an embodiment of the invention is administered as a bolus, which as used herein refers to the dosage being delivered in a time of less than ten minutes. In some embodiments a composition according to an embodiment of the invention is administered as an infusion, which as used herein refers to the dosage being delivered in a time of about ten minutes or greater.

Such injection may be made via a single needle, microneedle, or similar device, or an array of needles, microneedles, or similar devices. In some embodiments a composition according to an embodiment of the invention is delivered via a conventional syringe. In some embodiments, subdermal delivery is performed via a hollow microneedle injector. In some embodiments, subdermal delivery is performed a microneedle patch that has been coated with a composition according to an embodiment of the invention, for example that has been coated with a composition according to an embodiment of the invention by 3D printing. In some embodiments the composition is delivered via jet injector. The term "needle" as used herein refers to any such device for piercing the skin and injecting a composition according to an embodiment of the invention.

Preferably the composition is administered near the hair follicle of the patient. Accordingly, in some embodiments the composition is administered by injecting a therapeutic amount of composition in the dermis of the patient. In some embodiments the composition is administered by injecting a therapeutic amount of composition in the hypodermis of the patient. In some embodiments the composition is administered about 0.4 mm to about 2 mm into the patient's skin (i.e., about 0.4 mm to about 3 mm from the surface of the skin). In some embodiments the composition is administered about 0.4 mm, about 0.5 mm, about 0.6 mm, about 0.7 mm, about 0.8 mm, about 0.9 mm, about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, or about 3 mm into the patient's skin. In some embodiments the composition is administered between about 0.5 mm to about 1 mm, between about 1 mm to about 1.5 mm, between about 1.5 mm to about 2 mm, between about 2 mm to about 2.5 mm, between about 2.5 mm to about 3 mm, between about 1 mm to about 3 mm, between about 1.5 mm to about 3 mm, between about 0.4 mm to about 0.6 mm, between about 0.4 mm to about 0.8 mm, between about 0.4 mm to about 1 mm, between about 0.4 mm to about 1.2 mm, between about 0.4 mm to about 1.4 mm, between about 0.4 mm to about 1.6 mm, between about 0.4 mm to about 1.8 mm, between about 0.4 mm to about 2 mm, between about 0.4 mm to about 2.2 mm, between about 0.4 mm to about 2.4 mm, between about 0.4 mm to about 2.6 mm, between about 0.4 mm to about 2.8 mm, between about 0.4 mm to about 3 mm, between about 0.6 mm to about 0.8 mm, between about 0.6 mm to about 1 mm, between about 0.6 mm to about 1.2 mm, between about 0.6 mm to about 1.4 mm, between about 0.6 mm to about 1.6 mm, between about 0.6 mm to about 1.8 mm, between about 0.6 mm to about 2 mm, between about 0.6 mm to about 2.2 mm, between about 0.6 mm to about 2.4 mm, between about 0.6 mm to about 2.6 mm, between about 0.6 mm to about 2.8 mm, between about 0.6 mm to about 3 mm, between about 0.8 mm to about 1 mm, between about 0.8 mm to about 1.2 mm, between about 0.8 mm to about 1.4 mm, between about 0.8 mm to about 1.6 mm, between about 0.8 mm to about 1.8 mm, between about 0.8 mm to about 2 mm, between about 0.8 mm to about 2.2 mm, between about 0.8 mm to about 2.4 mm, between about 0.8 mm to about 2.6 mm, between about 0.8 mm to about 2.8 mm, between about 0.8 mm to about 3 mm, between about 1 mm to about 1.2 mm, between about 1 mm to about 1.4 mm, between about 1 mm to about 1.6 mm, between about 1 mm to about 1.8 mm, between about 1 mm to about 2 mm, between about 1 mm to about 2.2 mm, between about 1 mm to about 2.4 mm, between about 1 mm to about 2.6 mm, between about 1 mm to about 2.8 mm, between about 1 mm to about 3 mm, between about 1.2 mm to about 1.4 mm, between about 1.2 mm to about 1.6 mm, between about 1.2 mm to about 1.8 mm, between about 1.2 mm to about 2 mm, between about 1.2 mm to about 2.2 mm, between about 1.2 mm to about 2.4 mm, between about 1.2 mm to about 2.6 mm, between about 1.2 mm to about 2.8 mm, between about 1.2 mm to about 3 mm, between about 1.4 mm to about 1.6 mm, between about 1.4 mm to about 1.8 mm, between about 1.4 mm to about 2 mm, between about 1.4 mm to about 2.2 mm, between about 1.4 mm to about 2.4 mm, between about 1.4 mm to about 2.6 mm, between about 1.4 mm to about 2.8 mm, between about 1.4 mm to about 3 mm, between about 1.6 mm to about 1.8 mm, between about 1.6 mm to about 2 mm, between about 1.6 mm to about 2.2 mm, between about 1.6 mm to about 2.4 mm, between about 1.6 mm to about 2.6 mm, between about 1.6 mm to about 2.8 mm, between about 1.6 mm to about 3 mm, between about 1.8 mm to about 2 mm between about 1.8 mm to about 2.2 mm, between about 1.8 mm to about 2.4 mm, between about 1.8 mm to about 2.6 mm, between about 1.8 mm to about 2.8 mm, between about 1.8 mm to about 3 mm, between about 2.0 mm to about 2.2 mm, between about 2.0 mm to about 2.4 mm, between about 2.0 mm to about 2.6 mm, between about 2.0 mm to about 2.8 mm, between about 2.0 mm to about 3 mm, between about 2.2 mm to about 2.4 mm, between about 2.2 mm to about 2.6 mm, between about 2.2 mm to about 2.8 mm, between about 2.2 mm to about 3 mm, between about 2.4 mm to about 2.6 mm, between about 2.4 mm to about 2.8 mm, between about 2.4 mm to about 3 mm, between about 2.6 mm to about 2.8 mm, between about 2.6 mm to about 3 mm, or between about 2.8 mm to about 3 mm into the patient's skin.

In some embodiments a composition according to an embodiment of the invention can be administered in a plurality of injections. In some embodiments a composition according to an embodiment of the invention is administered in via about 1 injection/cm² skin to about 1000 injections/cm² skin, about 200 injections/cm² skin to about 800 injections/cm² skin, or about 400 injections/cm² skin to about 650 injections/cm² skin. In some embodiments a composition is administered via about 200 injections/cm² skin, about 250 injections/cm² skin, about 300 injections/cm² skin, about 350 injections/cm² skin, about 400 injections/cm² skin, about 450 injections/cm² skin, about 500 injections/cm² skin, about 550 injections/cm² skin, about 600 injections/cm² skin, or about 650 injections/cm² skin, Methods of Treatment A method of stimulating hair growth in a patient in need thereof includes administering a composition according to an embodiment of the present invention to the surface of or into the patient's skin. In some embodiments the composition is administered topically by applying the composition to the surface of the patient's skin. In some embodiments the composition is administered into the dermis or hypodermis of the patient's skin, for example, by injection as described herein.

In some embodiments, a composition according to an embodiment of the invention is administered to a patient's skin once a day for one day, once a day for one week, once a day for one month, once a day for one year, twice a day for one day, twice a day for one week, twice a day for one month, twice a day for one year, once a week for one week, once a week for one month, once a week for one year, twice a week for one week, twice a week for one month, twice a week for one year, once a month for one month, once a month for two months, once a month for six months, once a month for one year, twice a month for one month, twice a month for two months, twice a month for six months, twice a month for one year, once every two months for two months, once every two months for four months, once every two months for six months, once every two months for one year, once every three months for three months, once every three months for six months, once every three months for nine months, once every three months for one year, once every four months for four months, once every four months for eight months, once every four months for one year, once every six months for six months, once every six months for one year, or as needed.

EXAMPLES

Example 1. Injection of Hyaluronic Acid ("HA") at Concentrations of 100, 250, and 1000 µg/mL Three different concentrations (100, 250, and 1000 µg/mL) of "high" (molecular weight distribution greater than 950 kDa), "intermediate" (molecular weight distribution between 75-350 kDa), and "low" molecular weight (molecular weight distribution between 15-40 kDa) hyaluronic acid were each injected in mice. High molecular weight concentrations above 250 µg/mL were found to induce a strong inflammatory response, with 1000 µg/mL being the worst. For low molecular weight concentrations, the response was milder at 250 µg/mL compared to high molecular weight HA, but there was also strong inflammation at 1000 µg/mL. Adverse side effects were observed for all molecular weight hyaluronic acids at concentrations of 250 µg/mL and above.

Example 2. Injection of HA at Concentrations of 25, 50, and 100 µg/mL

Follow up experiments included lower HA concentrations (below 250 µg/mL). A small incision was done using a thin needle (insulin syringe) to facilitate injection. Three (3) microliters of either control, High (molecular weight distribution greater than 950 kDa), Intermediate (molecular weight distribution between 75-350 kDa), or Low molecular weight (molecular weight distribution between 15-40 kDa) hyaluronic acid were injected in the dorsal skin of P53 mice for three (3) consecutive days. In FIGS. 5-8, when looking at the back of the mouse with the mouse's head at the top, the control (1% BSA) injection is top left, the 25 µg/ml injection is top right, the 100 µg/ml injection is bottom right, and the 50 µg/ml injection is bottom left.

Figure 5:
FIG. 5 shows a mouse 18 days after injection with a control solution and 25, 50, and 100 mcg/mL solutions of low molecular weight hyaluronic acid.
Figure 6:
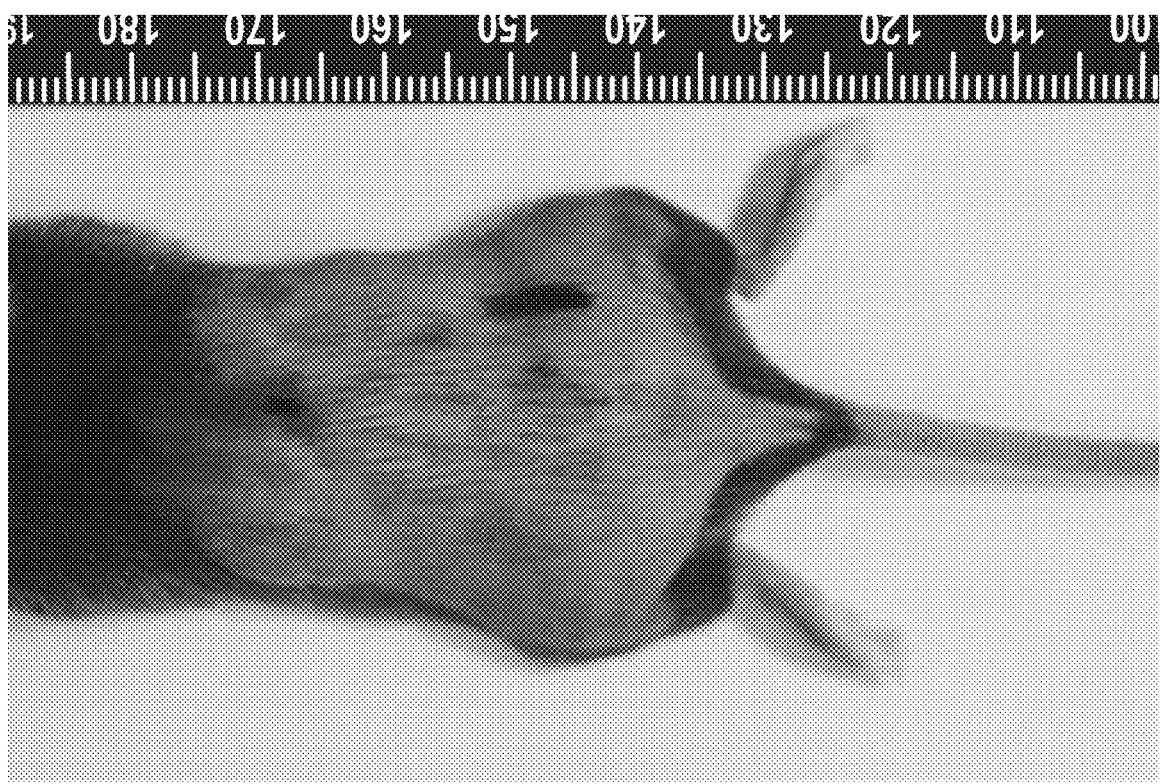
FIG. 6 shows a mouse 18 days after injection with a control solution and 25, 50, and 100 mcg/mL solutions of low molecular weight hyaluronic acid.
Figure 7:
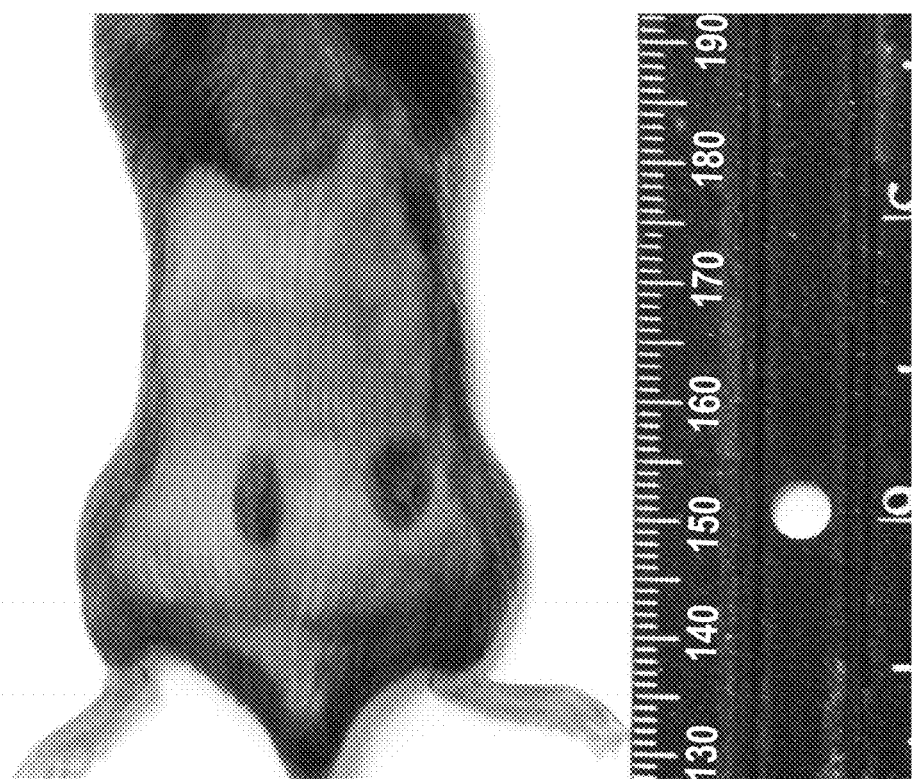
FIG. 7 shows a mouse 18 days after injection with a control solution and 25, 50, and 100 mcg/mL solutions of high molecular weight hyaluronic acid.
Figure 8:
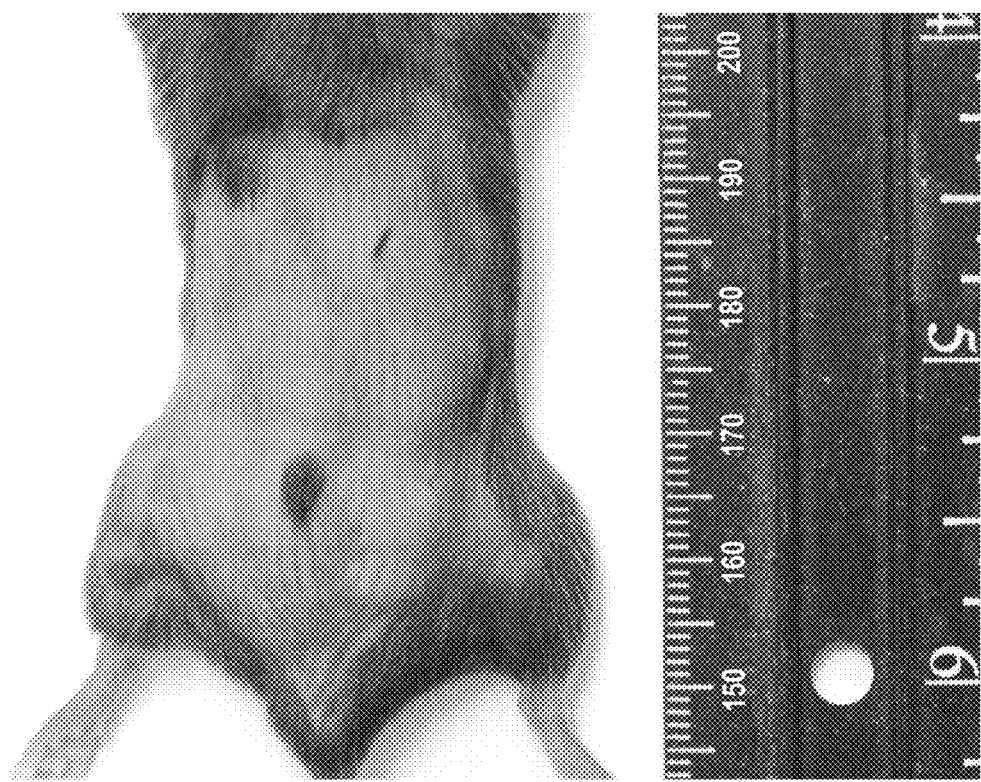
FIG. 8 shows a mouse 18 days after injection with a control solution and 25, 50, and 100 mcg/mL solutions of high molecular weight hyaluronic acid.

FIGS. 5 and 6 show representative images of two mice, each of which received injections of low molecular weight HA. FIGS. 7 and 8 show representative images of two mice, each of which received injections of high molecular weight HA. FIG. 5 shows growth in 25 µg/ml low molecular weight HA and 100 µg/ml low molecular weight HA spots. FIG. 6 shows growth in 25 µg/ml low molecular weight HA and 100 µg/ml low molecular weight HA spots. FIG. 7 shows growth in 50 µg/ml high molecular weight HA and 100 µg/ml high molecular weight HA spots. FIG. 8 shows growth in 25 µg/ml high molecular weight HA and 50 µg/ml high molecular weight HA spots.

For high molecular weight the injection site was monitored for 18 days for full anagen. In both high molecular weight HA and low molecular weight HA pigmentation was apparent at P14. Two mice had good induction for both low molecular weight HA and high molecular weight HA, but there was no induction on the intermediate weight HA. Without being bound by theory, the depth of the injection of the intermediate weight HA may have affected the strength of the induction.

FIGS. 7 and 8 show that high molecular weight HA induces at 50 µg/mL and 100 µg/mL without the massive inflammation response that was found in Example 1. In the case of low molecular weight HA, only 100 µg/mL induced hair growth. As shown in FIG. 6, low molecular weight HA mouse 2 has a nice anagen spot at 25 µg/mL (the control injection site is visible below it), but only in one mouse.

It will be appreciated by those skilled in the art that changes could be made to the exemplary embodiments shown and described above without departing from the broad inventive concepts thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and various features of the disclosed embodiments may be combined. Unless specifically set forth herein, the terms "a", "an" and "the" are not limited to one element but instead should be read as meaning "at least one".

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention.

We claim:

1. A method of stimulating hair growth in a skin of a patient in need thereof, comprising: administering to the skin of the patient a composition comprising hyaluronic acid in a concentration of about 1 mcg/mL to about 250 mcg/mL.

2. The method of claim 1, wherein the hyaluronic acid comprises an average molecular weight in a range of about 4,000 Da to 10,000 Da or in a range of about 20 KDa to 1350 KDa.

3. The method of claim 1, wherein the hyaluronic acid is cross-linked and optionally wherein the cross-linked hyaluronic acid density is about 20% or greater.

4. The method of claim 1, wherein the hyaluronic acid is present in a concentration of about 25 mcg/mL to about 250 mcg/mL.

5. The method of claim 1, wherein the hyaluronic acid is present in a concentration of about 50 mcg/mL to about 250 mcg/mL.

6. The method of claim 1, wherein the hyaluronic acid is present in a concentration of about 100 mcg/mL to about 250 mcg/mL.

7. The method of claim 1, wherein the hyaluronic acid has a concentration of about 100 ug/mL or less.

8. The method of claim 1, wherein the administering comprises injecting the composition into a dermal layer of the skin.

9. The method of claim 8, wherein the composition is injected about 400 microns to about 2 mm deep into the skin.

10. The method of claim 8, wherein the composition is administered in a plurality of injections in an amount of about 400 injections/cm$^2$ skin to about 650 injections/cm$^2$ skin.

11. The method of claim 1, further comprising applying iontophoresis to the skin.

12. The method of claim 1, further comprising applying electroporation to the skin.

13. The method of claim 1, further comprising applying laser ablation to the skin.

14. The method of claim 1, further comprising applying radiofrequency thermal ablation to the skin.

15. The method of claim 1, further comprising applying a microneedle device to the skin.

16. The method of claim 1, wherein the composition further comprises a CD44-binding ligand.

17. The method of claim 16, wherein the CD44-binding ligand is osteopontin.

18. A method of administering a composition for hair growth to a patient in need of treatment for hair loss comprising: injecting the composition into the skin of the patient, wherein the composition comprises hyaluronic acid in a concentration of about 1 mcg/mL to about 250 mcg/mL.

19. The method of claim 18, wherein the hyaluronic acid comprises an average molecular weight in a range of about 4,000 Da to 10,000 Da or in a range of about 20 KDa to 1350 KDa.

20. The method of claim 18, wherein the hyaluronic acid is cross-linked and optionally wherein the cross-linked hyaluronic acid density is about 20% or greater.

21. The method of claim 18, wherein the hyaluronic acid is present in a concentration of about 25 mcg/mL to about 250 mcg/mL.

22. The method of claim 18, wherein the hyaluronic acid is present in a concentration of about 50 mcg/mL to about 250 mcg/mL.

23. The method of claim 18, wherein the hyaluronic acid is present in a concentration of about 100 mcg/mL to about 250 mcg/mL.

24. The method of claim 18, wherein the hyaluronic acid has a concentration of about 100 ug/mL or less.

25. The method of claim 18, wherein the administering comprises injecting the composition into a dermal layer of the skin.

26. The method of claim 25, wherein the composition is injected via a needle, and wherein the needle is inserted 400 microns to about 2 mm into the skin before injection.

27. The method of claim 26, wherein the needle is a microneedle.

28. The method of claim 18, wherein the composition further comprises a CD44-binding ligand.

29. The method of claim 28, wherein the CD44-binding ligand is osteopontin.

* * * * *